United States Patent
Higo

(10) Patent No.: US 6,646,443 B2
(45) Date of Patent: Nov. 11, 2003

(54) ION CONCENTRATION METER

(75) Inventor: Yuji Higo, Tokyo (JP)

(73) Assignee: Organo Corporation, Tokyo (JP)

(*) Notice: Subject to any disclaimer, the term of this patent is extended or adjusted under 35 U.S.C. 154(b) by 26 days.

(21) Appl. No.: 09/980,048

(22) PCT Filed: Mar. 28, 2001

(86) PCT No.: PCT/JP01/02575

§ 371 (c)(1),
(2), (4) Date: Nov. 28, 2001

(87) PCT Pub. No.: WO01/75428

PCT Pub. Date: Oct. 11, 2001

(65) Prior Publication Data

US 2002/0158635 A1 Oct. 31, 2002

(30) Foreign Application Priority Data

Mar. 30, 2000 (JP) .......................................... 2000-93850

(51) Int. Cl.[7] .............................................. G01R 27/22
(52) U.S. Cl. ........................ 324/439; 324/442; 324/444
(58) Field of Search .......................... 204/228.6, 228.1, 204/232, 244; 324/441, 444, 447, 687, 691, 693, 696; 73/19.1, 19.01, 19.05, 31.07

(56) References Cited

U.S. PATENT DOCUMENTS 3,993,945 A * 11/1976 Warmoth et al. ............ 324/449
4,262,253 A * 4/1981 Clark .......................... 324/439
5,223,796 A * 6/1993 Waldman et al. ............ 324/687
5,651,894 A * 7/1997 Boyce et al. ................ 210/652
6,264,825 B1 * 7/2001 Blackburn et al. ....... 205/777.5

* cited by examiner

Primary Examiner—Jay Patidar
Assistant Examiner—Vincent Q. Nguyen
(74) Attorney, Agent, or Firm—Norris McLaughlin & Marcus

(57) ABSTRACT

Two conductivity measuring cells each having at least two electrodes are arranged in series in a flow path of a sample to be measured so that the sample may make contact with the cells in sequence. A difference conductivity meter produces the difference between the signals themselves detected by the conductivity cells as the difference in conductivity of the sample between the positions of the conductivity measuring cells. Based on the predetermined correlation between the change in conductivity of the sample and the change in concentration of the ion of interest in the sample, an ion concentration meter thus constructed derives the change in ion concentration of the sample from the output from the difference conductivity meter. The ion concentration meter can measure a minute change in ion concentration, such as of ammonia, with extremely high accuracy and sensitivity, while carrying out continuous measurement.

20 Claims, 14 Drawing Sheets

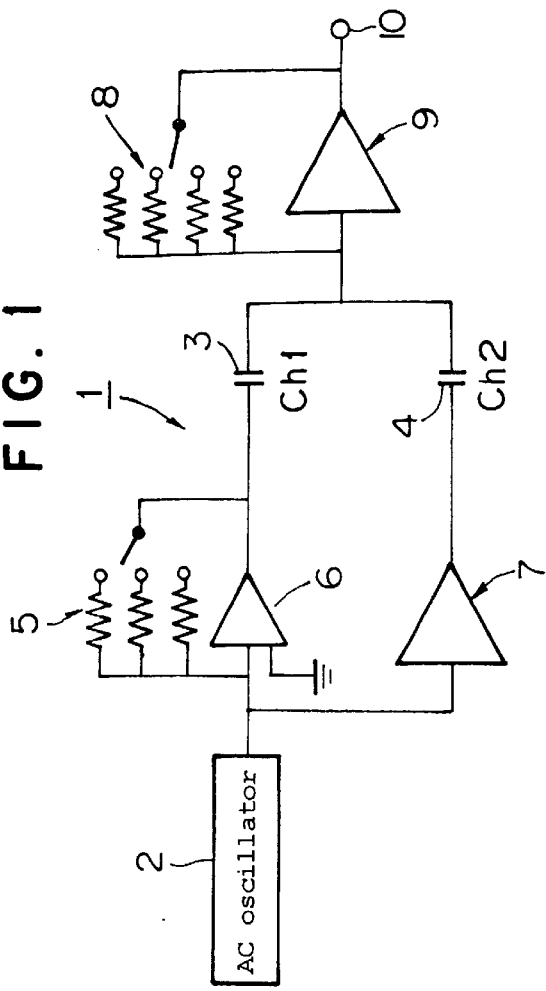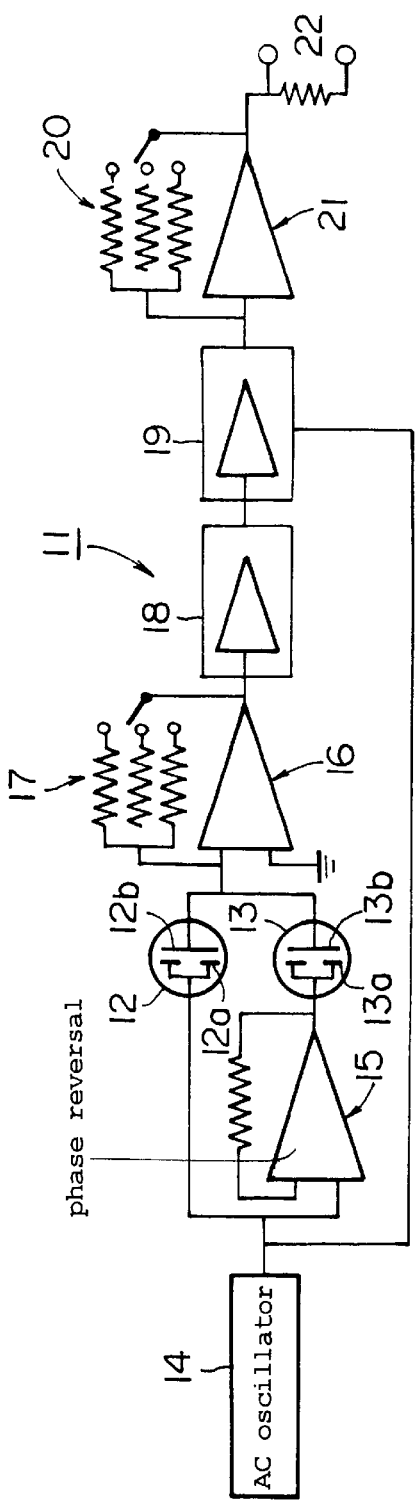

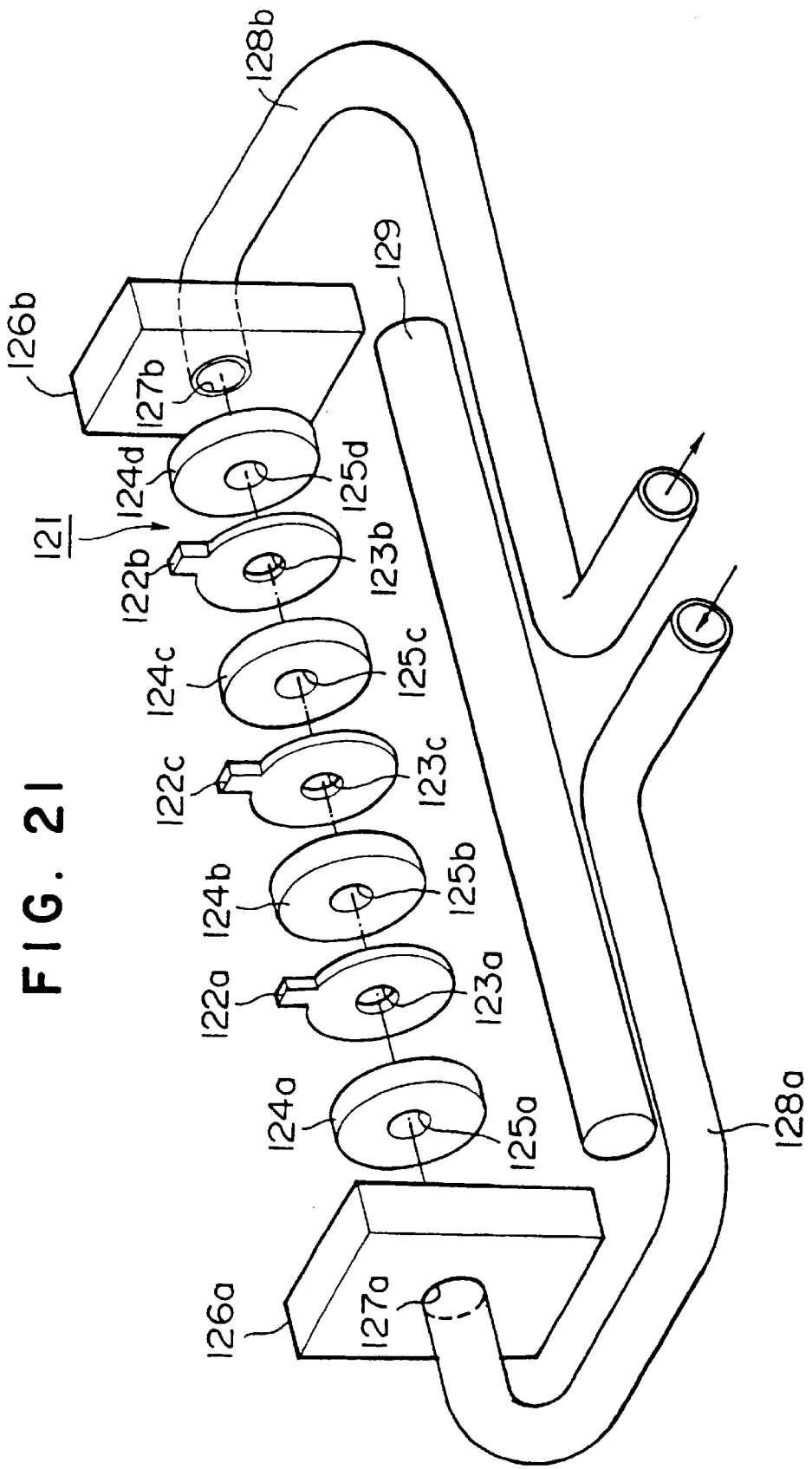

ION CONCENTRATION METER

This application is a 371 of PCT/JP01/02575, filed on Mar. 28, 2001.

TECHNICAL FIELD OF THE INVENTION

The present invention relates to an ion concentration meter, and specifically, relates to an ion concentration meter which can measure a minute change in ion concentration at an extremely high accuracy and which is suitable for detection of a change in ion concentration, a leakage of ions or the like in various apparatuses or various systems.

BACKGROUND ART OF THE INVENTION

Measurement of the concentrations of ammonium, sodium, chloride, calcium, potassium, carbonate, silica, magnesium, sulphate ions and the like may be required in various industrial fields. For example, in a cooling water producing system, as described later, heat exchange is carried out between the side of a refrigerator and brine used for respective use points by a heat exchanger, and the cooled brine is stored in respective target tanks and used as cooling water at the respective use points. In such a system, particularly, because leakage of ammonia from the refrigerator side into the brine through the heat exchanger, etc. poses a problem, it is required to measure and monitor the concentration of the ammonia which has leaked into the brine. It is known that the concentration of ammonia in a sample has a correlation with the conductivity of the sample, and that it is effective to measure the conductivity of the sample for determining the concentration of ammonia.

Generally, in a conventional method for measuring a concentration of ammonia in a sample, for example, an aliquot amount of sample is collected for measurement, ammonia in the sample is evaporated by heating or using a strong alkali and the evaporated ammonia is trapped in deionized water, and the concentration of ammonia and the change of the concentration are detected by measuring a change in conductivity of water. In this method, sampling, cleaning, water for trapping, etc. are necessary, and there is a possibility that an apparatus for this method may become extremely expensive for achieving a high-accuracy measurement though it depends upon the performance of a conductivity meter.

Further, in a case where a conventional-type conductivity meter is used and when a base conductivity of a sample is very great, it is impossible to detect a minute change in concentration of ammonia. For example, assuming that the conductivity of a sample having a base conductivity of 3000 $\mu S$ is changed by an amount of 0.5 $\mu S$ by adding ammonia, the ratio of change in conductivity is about $1/6000$, and it is impossible to measure such a change by a conventional-type conductivity meter in view of its noise level. Therefore, if a sample ion is absorbed to a low-conductivity water such as deionized water and 1 $\mu S$ water is prepared for example, because the above-described change becomes about $1/2$, detection may be possible. However, because such a measuring method is carried out at a repeated batch sampling formation, equipment and reagent therefor are required, and the measuring apparatus becomes expensive as well as the measuring operation becomes troublesome. Moreover, it is difficult to continuously measure the change in concentration.

DISCLOSURE OF THE INVENTION

Accordingly, an object of the present invention is to provide an ion concentration meter which can measure a change in ion concentration, such as of ammonia, with extremely high accuracy and sensitivity, which also can carry out continuous measurement, and which has a simple structure and can be manufactured at a low cost.

To accomplish the above object, an ion concentration meter according to the present invention comprises a difference conductivity meter wherein two conductivity measuring cells each having at least two electrodes are arranged in series in a flow path of a sample to be measured so that the sample being sent may make contact with the cells in sequence, the difference conductivity meter produces a difference between signals themselves detected by the conductivity measuring cells as a difference in conductivity of the sample between the positions of the conductivity measuring cells, and the ion concentration meter derives a change in ion concentration of the sample from the output from the difference conductivity meter, based on a predetermined correlation between a change in conductivity of the sample and a change in concentration of an ion to be detected in the sample.

In the present invention, although the ion to be detected is not particularly restricted, as ions capable of being effectively detected, at least one selected from the group consisting of ammonium, sodium, chloride, calcium, potassium, carbonate, silica, magnesium and sulphate ions can be cited.

In this ion concentration meter, it is preferred that a time delay column having a predetermined capacity is interposed between the above-described two conductivity measuring cells arranged in the flow path of the sample to be measured. Namely, at a condition where a time difference set by the time delay column is given, a difference between signals themselves detected by both conductivity measuring cells is produced, and based on the output, the change in ion concentration is measured. Although directly it is detected as a change in conductivity of a sample, since the correlation between a change in conductivity of the sample and a change in concentration of an ion to be detected in the sample has been determined in advance, by reading or by using a simple calculating means (a calculation program) based on the correlation, a change in ion concentration of the sample is easily derived.

Further, in the ion concentration meter, it is preferred that a degasifier capable of degasifying and defoaming the sample being sent is disposed upstream of the two conductivity measuring cells arranged in the flow path of the sample to be measured. By this, any influence of micro bubbles and the like on the measurement can be removed.

Further, the ion concentration meter can further comprise means for sending a sample to be measured with respect to a change in ion concentration to the flow path of the sample to be measured, and means for injecting a standard raw liquid into the sample to be measured with respect to a change in ion concentration. In such a structure, because it is possible to always compare the ion concentration of the sample with the standard raw liquid, for example, even if a change in ion concentration of the sample to be measured exhibits to be extremely minute during a short period of time and it is difficult to detect the minute change, in a case where the change is continued, when the change in ion concentration becomes more than a certain level after a certain time, the change can be surely detected. Further, a structure also can be employed for the ion concentration meter wherein a standard raw liquid, for example, a standard raw liquid having a constant ion concentration or substantially containing no ion is used as a carrier fluid, means for sending the carrier fluid to the flow path of the sample to be measured is provided, and while the sample to be measured with respect to a change in ion concentration is injected into the carrier fluid, the change in ion concentration of the sample is measured. In such a structure, because it is possible to always compare the ion concentration of the sample with the standard raw liquid, for example, even if a change in ion concentration of the sample to be measured exhibits to be extremely minute during a short period of time and it is difficult to detect the minute change, in a case where the change is continued, when the change in ion concentration becomes more than a certain level after a certain time, the change can be surely detected.

Further, the ion concentration meter also can be structured so as to further comprise means for switching a plurality of sample sources and sending a sample from a selected sample source to the flow path of the sample to be measured. In this structure, the path of the sample to be measured having the above-described two conductivity measuring cells can be disposed for each of the plurality of sample sources. Whichever structure is to be employed may be decided depending on the frequency or interval of measurement, the necessity of continuous measurement, etc.

Although the structure of the conductivity measuring cell itself is not particularly restricted, the following structures can be employed. For example, a structure can be employed wherein the above-described at least two electrodes in each conductivity measuring cell comprise a conductivity detection electrode and an electric current supply electrode. Alternatively, another structure can be employed wherein each of the conductivity measuring cells has three electrodes, the three electrodes include a conductivity detection electrode and two AC current supply electrodes disposed on both sides of the conductivity detection electrode at respective distances, and an AC current of the same phase is applied to the two AC current supply electrodes. Alternatively, a further structure can be employed wherein each of the conductivity measuring cells has three electrodes, the three electrodes include a conductivity detection electrode, an AC current supply electrode disposed on one side of the conductivity detection electrode at a distance, and a grounded electrode disposed on the other side of the conductivity detection electrode at a distance.

In such conductivity measuring cells, it is preferred that the above-described at least two electrodes are constructed so that their electrode surfaces are formed by titanium oxide layers on electrode bodies made of a conductive metal. In such a constitution, when organic substances and the like are contained in a sample to be measured, the property for decomposing organic substances based on the photocatalytic activity of the titanium oxide, and its super-hydrophilicity can be effectively utilized, in order to eliminate adverse effects on the measurement of the conductivity due to the adhesion or adsorption of the organic substances to the electrode surfaces. It is preferred that light irradiating means is disposed against the titanium oxide layers to provide a photocatalytic activity to the titanium oxide layers. For example, each conductivity measuring cell can be constructed so as to have a space for storing a substance to be measured defined between respective electrode surfaces of the above-described at least two electrodes, and light irradiating means that irradiates light onto the respective electrode surfaces.

In the conductivity measuring cells, it is preferred that light irradiated by the above-described light irradiating means has a wavelength which brings about a photocatalytic activity of the above-described titanium oxide layers. For example, light with a wavelength from about 300 to about 400 nm can be employed. As the light irradiating means, a light source composed of means for irradiating ultraviolet rays and the like such as a black light may be directly employed, and a light guiding material (for example, an optical fiber) to guide light from a light source provided as means for irradiating light may also be employed.

Further, the above-described space for storing a substance to be measured may be defined by a light transmitting material, and it may be constituted so that the light from the light irradiating means is irradiated onto an electrode surface through the light transmitting material (for example, glass). In this case, if a titanium oxide coating layer capable of transmitting light is provided on the surface of the light transmitting material at its side facing the space for storing a substance to be measured (a surface in contact with solution), adhesion of organic substances and the like to this surface of the light transmitting material can be prevented by super-hydrophilicity and organics decomposition property ascribed to the titanium oxide layer.

The above-described electrode can be produced by, for example, the following method. Namely, a method can be employed wherein an electrode surface is formed by providing on a titanium oxide layer on a surface of an electrode body made of a conductive metal by a surface treatment such as sputtering, plating or the like. Alternatively, a method can also be employed wherein an electrode surface made of a titanium oxide layer is formed by providing oxygen to a surface of an electrode body made of titanium. As the method for forming a titanium oxide layer by providing oxygen, a method based on air oxidation other than a method utilizing electrolysis can be employed.

Such an ion concentration meter according to the present invention is suitable for application to the measurement of a change in ion concentration of a fluid to be heat exchanged in a heat exchange system, or for application to the measurement of a change in ion concentration of a liquid diluted or mixed. Further, the ion concentration meter according to the present invention is suitable for application to a cooling water producing system. For example, the ion concentration meter can be constituted as a meter wherein the sample is collected from a brine in a cooling water producing system, and the ion concentration meter measures a change in concentration of ammonia which has leaked from the side of a refrigerator into the brine.

In the ion concentration meter according to the present invention, basically, not an absolute value of a conductivity of a sample but a change in conductivity is measured, and the measured change in conductivity is determined as a value corresponding to a change in ion concentration. Since a value of a change is detected, an extremely high-accuracy measurement becomes possible in spite of a large base value of the conductivity or the ion concentration. Further, since a sample can be directly measured, equipment and reagent for the measurement at a repeated batch sampling formation as in the conventional method are not required, and therefore, the measuring apparatus and the operation can be both simplified. Furthermore, if the electrodes utilizing the photocatalytic activity of titanium oxide are used, a stable measurement can be possible.

BRIEF EXPLANATION OF THE DRAWINGS

FIG. 1 is a schematic circuit diagram showing an example of the structure of a difference conductivity meter used in an ion concentration meter according to the present invention.

FIG. 2 is a schematic circuit diagram showing another example of the structure of a difference conductivity meter used in an ion concentration meter according to the present invention.

FIG. 21 is an exploded perspective view showing another example of the mechanical constitution of a conductivity measuring cell usable for an ion concentration meter according to the present invention.

THE BEST MODE FOR CARRYING OUT THE INVENTION

Figure 3:
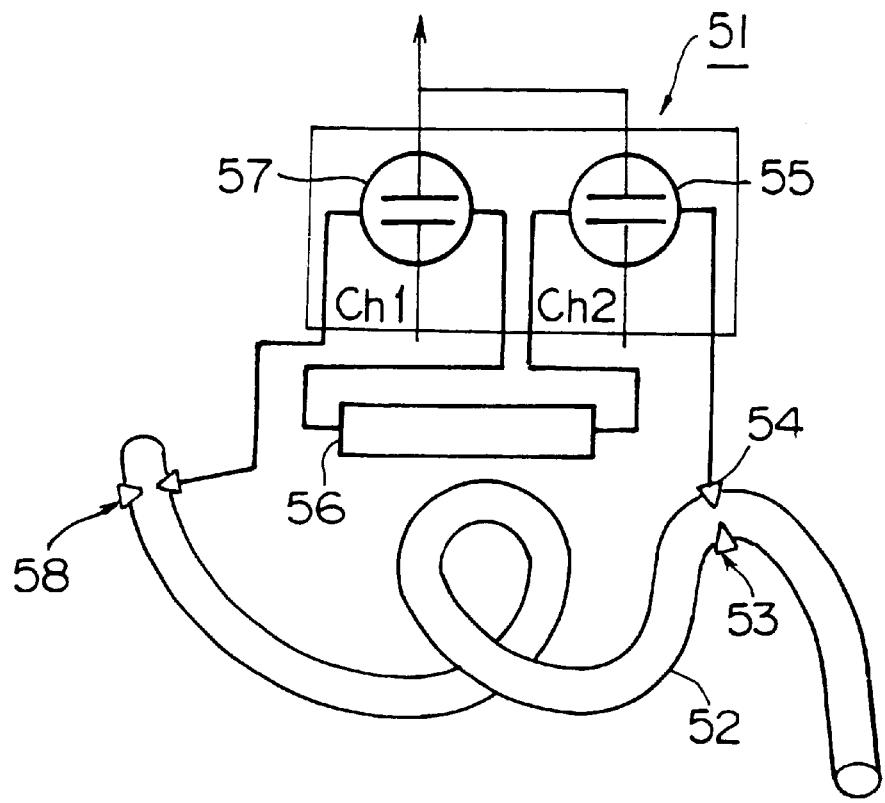
FIG. 3 is a schematic view showing an example of use of a difference conductivity meter with a time delay column used in an ion concentration meter according to the present invention.

Hereinafter, more detailed technical concept of the present invention and preferred embodiments of the present invention will be explained referring to Figures.

First, a difference conductivity meter used in an ion concentration meter according to the present invention will be explained, next, the ion concentration meter according to the present invention will be explained mainly as to experiments for confirming the effectiveness of use of the difference conductivity meter for the measurement of ion concentration, and further, examples of the constitutions when the ion concentration meter is applied to concrete fields will be explained.

Firstly, a difference conductivity meter used in an ion concentration meter according to the present invention will be explained. The difference conductivity meter used in the present invention is a difference conductivity meter wherein two conductivity measuring cells each having at least two electrodes are arranged in series in a flow path of a sample to be measured so that the sample being sent may make contact with the cells in sequence, the difference conductivity meter produces a difference between signals themselves detected by the conductivity measuring cells as a difference in conductivity of the sample between the positions of the conductivity measuring cells.

FIG. 1 shows an example of the difference conductivity meter used in an ion concentration meter according to the present invention. In the difference conductivity meter 1 shown in FIG. 1, an AC current from an AC oscillator 2 is supplied to the respective conductivity measuring cells 3, 4. The AC current, which is amplified by a phase reversing amplifier 6 with a magnification setting unit 5 at a predetermined magnification and the phase of which is reversed, is supplied to one conductivity measuring cell 3, To the other conductivity measuring cell 4, an AC current amplified at a constant magnification by an amplifier 7 is supplied without reversing its phase. The output sides of the respective conductivity measuring cells 3, 4 are connected to each other, and since the phase of the above-described one AC current supplied is reversed, a subtraction treatment is conducted to create a difference between the sensing signals themselves sent from both of the conductivity measuring cells 3, 4. This subtraction treated signal is amplified by an amplifier 9 with a sensitivity (measuring range) switching unit 8, and output as a single output signal 10. Therefore, this output signal 10 indicates a difference or variation between the detected conductivities of both of the conductivity measuring cells 3, 4.

Thus, since the difference or the variation is not calculated from the absolute values of the sensing signals output from the respective conductivity measuring apparatuses, but the subtraction treatment is carried out with respect to the sensing signals themselves from the respective conductivity measuring cells 3, 4 in a single difference conductivity meter 1, only the difference or variation between conductivities of both of the conductivity measuring cells 3, 4 can be extracted accurately. Further, because the measuring range at the time of this measurement may be adjusted not relative to the absolute value of conductivity but relative to the difference or variation of conductivity to be detected, even if the difference or variation is much smaller than the absolute value of conductivity, the adjustment to an optimum measuring range regardless of the absolute value of conductivity is possible, and an extremely high-accuracy and high-sensitivity measurement becomes possible.

Further, since the level of the current supplied to one electric conductivity measuring cell 3 can be appropriately switched by the magnification switching unit 5, an optimum adjustment of sensitivity can be performed for any of a concentration system or a dilution system. Moreover, since the sensitivity (measuring range) switching unit 8 is provided also on the output side, the level of the signal finally output can also be adjusted to an optimum level, and the data of the difference or variation of conductivity can be determined at an optimum sensitivity. As a result, extremely high-reliability data of the difference or variation in the conductivity measurement can be obtained with a high accuracy and a high sensitivity.

Such a difference conductivity meter can also be constituted as shown in FIG. 2 for example. In FIG. 2, a difference conductivity meter 11 has at least two conductivity measuring cells (in this embodiment, a two-cell constitution is depicted) each having at least two electrodes (in this embodiment, a three-electrode constitution is depicted) brought into contact with a substance to be measured (a sample). In this embodiment, the conductivity measuring cells 12, 13 are connected electrically so that sensing signals themselves from the conductivity measuring cells 12, 13 can be treated to be subtracted.

The conductivity measuring cells 12, 13 are connected electrically in parallel with each other, and an AC current with the same phase is supplied from an AC oscillator 14 provided as a power source to electric current supply electrodes 12a, 13a of the respective conductivity measuring cells 2, 3. The conductivity detection electrodes 12b, 13b of the respective conductivity measuring cells 12, 13 are electrically connected to each other, and the detection signals themselves from the conductivity detection electrodes 12b, 13b are subtracted as follows. A phase reversing unit 15 capable of amplifying or attenuating the supplied AC current at a predetermined magnification is provided before the conductivity detection electrode 13a of the conductivity measuring cell 13, and the level of a conductivity of a substance to be measured as an object detected by the conductivity measuring cell 13 is made different from that by the conductivity measuring cell 12, as well as the phase of the sensing signal is reversed. By this, the sensing signals themselves from the respective conductivity measuring cells 12, 13 are substantially subtracted.

The signal obtained after the above-described treatment of the electric calculation, namely, the signal obtained from a coupled point of the conductivity detection electrodes 12b, 13b, is amplified to an appropriate level suitable as an output signal, by a single amplifier 16. At this juncture, an optimum measuring range can be selected depending upon the measurement object by a measuring range switching unit 17.

In this embodiment, the signal sent from amplifier 16 is synchronized with the output side of the AC current oscillator 14 by a synchronous rectifier 19, after a temperature compensation for the measurement environment is carried out by a temperature compensator 18. Further, the signal is amplified by an amplifier 21 with a range controller 20 so as to become a signal with an optimum level for a certain kind of control or display of output, and it is extracted as an actual output 22.

In the above-described difference conductivity meters, a change in conductivity of a sample (a substance to be measured) with time can be accurately determined by using a time delay column. For example, as shown in FIG. 3, when a change in conductivity between different positions is measured in the flow direction of the water flowing in a water flow tube 52, a difference conductivity meter 51 is disposed to take out a sample water through, for example, a Venturi tube 54 at an upstream position 53. After the conductivity of this sample water is at first detected by one conductivity measuring cell 55, the sample water is sent to the other conductivity measuring cell 57 through a time delay column 56, the conductivity of the sample water is measured again in this cell 57, and the sample water after the measurement is returned to a downstream position 58 of the water flow tube 52. The time delay column 56 is designed to adjust a residual time from an end of inlet to an end of outlet by, for example, winding a capillary spirally, and in this embodiment, the residual time is adjusted to substantially correspond to a flow time from the upstream position 53 to the downstream position 58 of the water flow tube 52.

By providing such a time delay column 56 and timely shifting the timing of conductivity detection as to an identical sample water, it can be observed how the conductivity varies between these two different times. And, by employing the difference conductivity meter 51 according to the present invention for this observation, the change in conductivity is detected with a high reliability, a high accuracy and a high sensitivity.

In the present invention, the structures of the respective conductivity measuring cells themselves are not particularly restricted, and they may be each constructed to have at least two electrodes brought into contact with a substance to be measured (a sample). In the case where two electrodes are used in each conductivity measuring cell, one is a conductivity detection electrode and the other is a electric current supply electrode, and when three-electrode constitution is employed, one of the three electrodes can be formed as a grounded electrode. Although it is preferred that an AC current is supplied to the electric current supply electrode, a constitution for supplying a DC current can also be employed.

Figure 4:
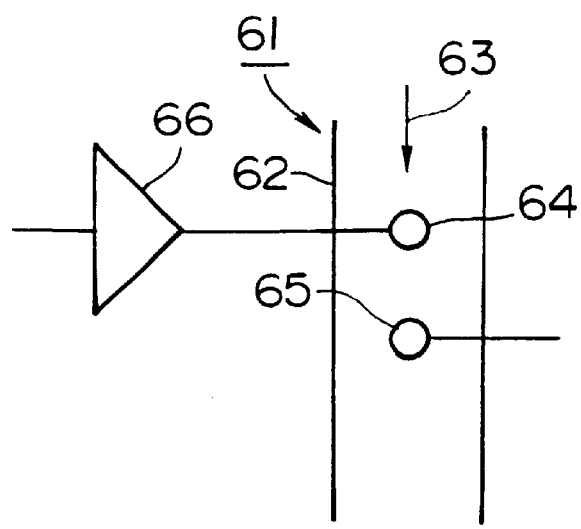
FIG. 4 is a schematic diagram showing an example of a conductivity measuring cell usable for a difference conductivity meter in the present invention.

FIG. 4 shows a schematic constitution of a conductivity measuring cell having a two-electrode formation applicable to the present invention. In the conductivity measuring cell 61 shown in FIG. 4, a power supply electrode 64 and an electric conductivity detection electrode 65 are disposed at a distance in a fluid 63 to be measured and flowing in a measurement tube 62 or being stored in the tube 62. An AC current is applied to the power supply electrode 64 from, for example, a power source not shown) through an amplifier 66, and a detection current from the conductivity detection electrode 65 receives the treatment of the aforementioned subtraction.

In the conductivity measuring cell 61 of two-electrode formation as described above, the measurement tube 62 is composed of an insulation material (for example, a vinyl chloride tube) at least at the position of the above-described conductivity measurement, since the system is often substantially in a grounded condition at any position of the extending portion of the tube, noises may be picked up from the environment, originating from the grounded condition.

Figure 5:
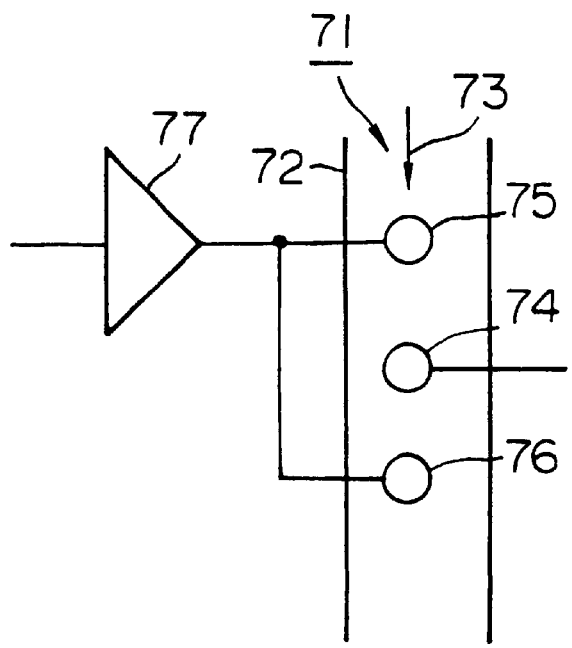
FIG. 5 is a schematic diagram showing another example of a conductivity measuring cell usable for a difference conductivity meter in the present invention.
Figure 6:
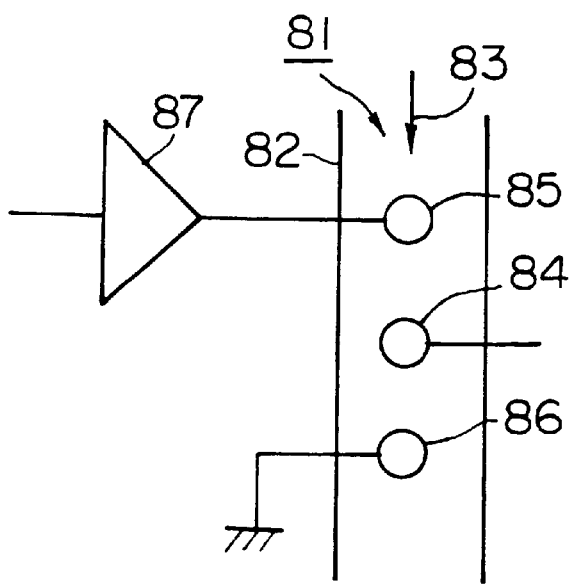
FIG. 6 is a schematic diagram showing a further example of a conductivity measuring cell usable for a difference conductivity meter in the present invention.

In order to remove any effect ascribed to such noises, it is preferred that conductivity measuring cells having three-electrode constitutions, for example, as shown in FIGS. 5 and 6, are used. In a conductivity measuring cell 71 shown in FIG. 5, three electrodes 74, 75, 76 brought into contact with a fluid 73 to be measured are provided in the fluid 73 to be measured and flowing in an insulated measurement tube 72 or being stored in the measurement tube 72. The three electrodes comprise a conductivity detection electrode 74 for detecting conductivity and two AC current supply electrodes 75, 76 disposed on both sides of the conductivity detection electrode 74 at respective distances. AC current of the same phase is applied with a constant voltage and the same potential to the two AC current supply electrodes 75, 76 through an amplifier 77. The detected current from the conductivity detection electrode 74 receives the treatment of the aforementioned subtraction.

In the conductivity measuring cell 71 shown in FIG. 5, the conductivity measuring electrode 74 is electrically shielded against a grounded point which would exist at any point of the extending portion of the measurement tube 72 by the two AC current supply electrodes 75, 76, which are disposed on both sides of the conductivity detection electrode 74, and to which an AC current of the same phase is supplied. Namely, since a constant voltage AC current with the same phase is applied to the two AC current supply electrodes 75, 76, and the potential difference between the conductivity detection electrode 74 and the AC current supply electrode 75, 76 is always maintained at a predetermined constant value, substantially no electric resistance exists between the conductivity detection electrode 74 and an outside grounded point. Therefore, any resistance between a conductivity detection electrode and an outside grounded point, and any influence on an output electric current from the conductivity detection electrode originating from a variation of any such resistance, as in the cell constitution shown in FIG. 4, disappear substantially completely. In other words, any leaked electric current from the conductivity detection electrode 74 to the outside grounded point does not exist at all. As a result, the output electric current from the conductivity detection electrode 74 is extracted at a condition with no disturbance at all times, and dispersion and variation due to the disturbance are prevented, thereby ensuring a stable and high-accuracy measurement of conductivity at all times.

In the conductivity measuring cell 81 shown in FIG. 6, three electrodes 84, 85, 86 brought into contact with a fluid 83 to be measured are provided in the fluid 83 flowing in an insulated measurement tube 82 or being stored in the measurement tube 82. The three electrodes comprise a conductivity detection electrode 84 for detecting conductivity and an AC current supply electrode 85 disposed on one side of the conductivity detection electrode 84 at a distance, and a grounded electrode 86 disposed on the other side of the conductivity detection electrode 84 at a distance. An AC current with a predetermined phase is applied at a constant voltage to the AC current supply electrode 85 through an amplifier 87. The detected current from the conductivity detection electrode 84 receives the treatment of the aforementioned subtraction.

In the conductivity measuring cell 81 shown in FIG. 6, an AC current with a constant voltage is supplied only to the AC current supply electrode 85, the grounded electrode 86 is forcibly made to be zero in potential by the grounding, and these electrodes 85, 86 are disposed on both sides of the conductivity detection electrode 84. Therefore, the portion between the electrodes 85, 86 is divided in electrical circuit in a formation of a so-called resistive division, by the conductivity detection electrode 84. In the circuit between these electrodes 85, 86, a predetermined AC current with a constant voltage is applied to the electrode 85, and the potential of the electrode 85 is always forced to be zero, and this condition is always maintained stably. Namely, even if any extending portion of the measurement tube 82 is grounded, there is no room to allow a resistance to enter between the grounded point and the conductivity detection electrode 84, thereby preventing the electric current extracted from the conductivity detection electrode 84 from shifting or varying. Therefore, the output electric current from the conductivity detection electrode 84 is extracted at a condition with no disturbance at all times, and dispersion and variation due to the disturbance are prevented, thereby ensuring a stable and high-accuracy measurement of conductivity at all times.

Figure 7:
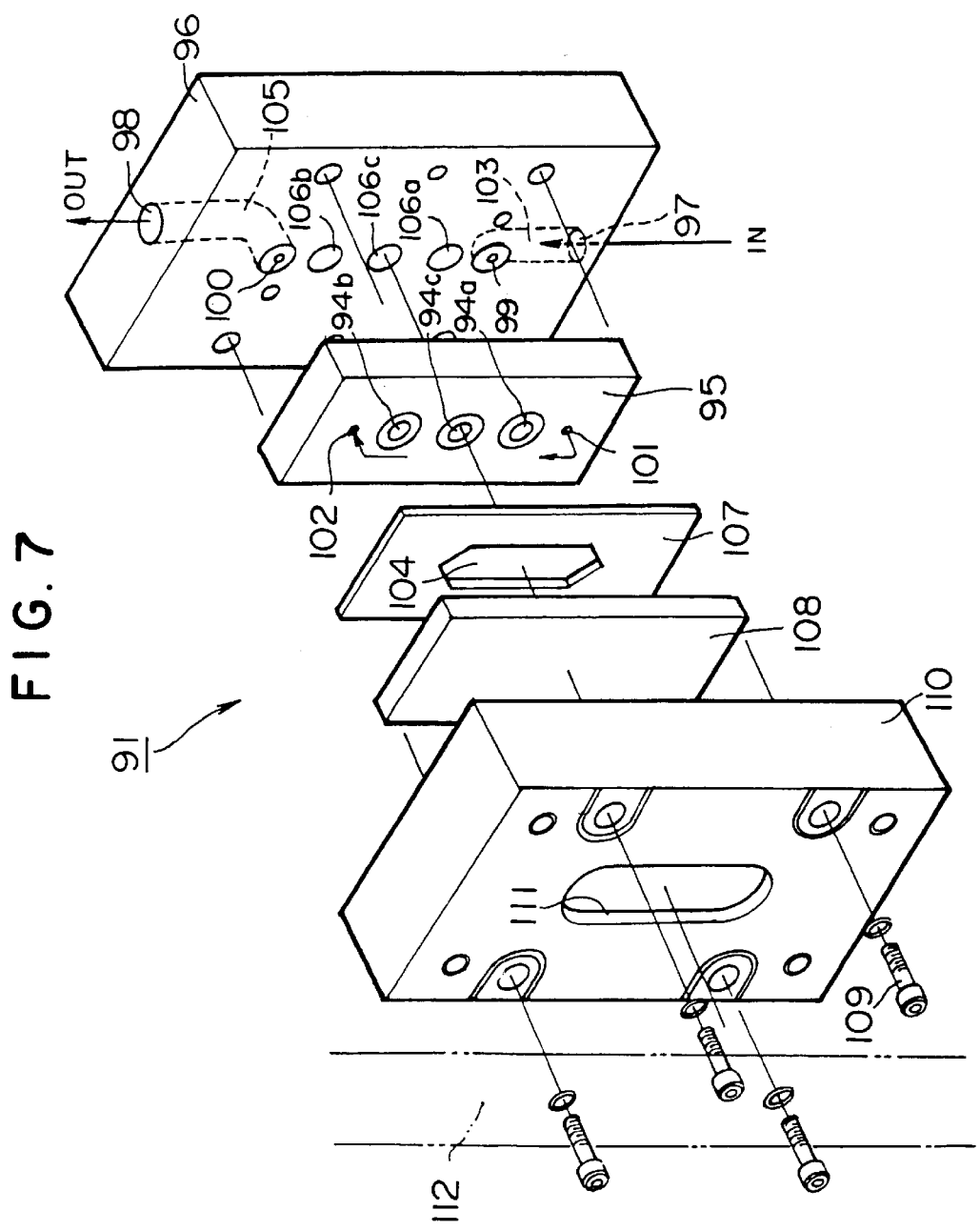
FIG. 7 is an exploded perspective view showing an example of the mechanical constitution of a conductivity measuring cell usable for a difference conductivity meter in the present invention.
Figure 8:
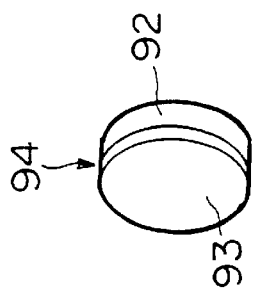
FIG. 8 is a perspective view showing an example of the constitution of an electrode of a conductivity measuring cell usable for a difference conductivity meter in the present invention.

In the present invention, the mechanical construction of a conductivity measuring cell is not particularly restricted, and it can be formed as a construction shown in FIG. 7 for example. In the conductivity measuring cell 91 shown in FIG. 9, a conductivity measuring electrode 94 shown in FIG. 8 is preferably used for example, wherein an electrode surface is formed by a titanium oxide layer 93 on the surface of an electrode body 92 made of a conductive metal. The titanium oxide layer 93 is formed by a surface treatment such as sputtering, plating and the like, or is formed by oxidizing the surface of the electrode body 92 made of a titanium metal. The oxidation is conducted by electrolysis or air oxidation.

The conductivity measuring electrodes 94 are used as electrodes corresponding to two or three electrodes shown in FIGS. 4 to 6, and are attached to an electrode holder 95 made of an insulation material in a condition where the electrode surfaces are exposed as shown in FIG. 7. Three electrodes 94 are disposed in a raw, and the electrodes 94a and 94b at both sides constitute AC current supply electrodes connected to a power source, and the electrode 94c at the central position constitutes an detection electrode functioning as a sensor for detecting electric conductivity.

Electrode holder 95 is fixed at a predetermined position of a substrate 96. In the substrate 96, inlet 97 for introducing a fluid to be measured (for example, an aqueous solution), outlet 98 for discharging the fluid, and flow holes 99 and 100 for measuring conductivity are provided. In the electrode holder 95, flow holes 101 and 102 are provided, and the flow hole 101 is disposed to communicate with the flow hole 99 of the substrate, and the flow hole 102 is disposed to communicate with flow hole 100 of the substrate, respectively. A fluid to be measured introduced from inlet 97 is sent into a space 104 for storing a substance to be measured, which is defined on the side of the electrode surfaces of the respective electrodes 94 through an inside path 103 of the substrate 96, the flow hole 99, and the flow hole 101 of electrode holder 95. The space 104 for storing a substance to be measured forms a flow path for measuring conductivity of a fluid to be measured. The fluid from the space 104 for storing a substance to be measured is discharged from outlet 98 through the flow hole 102 of electrode holder 95, the flow hole 100 of the substrate 96, and an inside path 105.

In the substrate 96, through holes 106a, 106b, 106c are opened at positions corresponding to the respective electrodes 94a, 94b, 94c, and necessary electric wires are pulled out of the through holes 106a, 106b, 106c.

The space 104 for storing a substance to be measured, in this embodiment, is defined by a sheet-like packing 107, and a transparent glass plate 108 provided as a light transmitting material which is disposed to confront electrode holder 95 with a gap via packing 107. It is preferred that a titanium oxide coating layer is provided to such an extent that the light transmitting property is not damaged, also to the surface of glass plate 108 on its side facing the space 104 for storing a substance to be measured. The conductivity of the fluid, flowing in this space 104 for storing a substance to be measured, is measured.

Electrode holder 95, packing 107 and glass plate 108 are fixed to a cover body 110 on one surface side of substrate 96 by bolts 109. A window 111 for transmitting light is opened on cover body 110. Through this window 111, light from light irradiating means 112 which is disposed outside is irradiated. Light irradiated is shed on titanium oxide layers 93 that form the electrode surfaces of the respective electrodes 94a, 94b, 94c through glass plate 108 from the window 111. Light having a wavelength that brings about a photocatalytic activity of titanium oxide layers 93 is selected as the light to be irradiated. For example, an ultraviolet ray with a specified wavelength (for example, a wavelength falling within a range of 300 to 400 nm) can be employed, and as light irradiating means 112, a black light that irradiates ultraviolet rays for example, can be used.

If such a conductivity measuring cell 91 is constituted, by irradiating light from light irradiating means 112, titanium oxide layers 93 provided on the surfaces of the respective electrodes 94a, 94b, 94c exhibit a photocatalytic activity, and even when organic substances are contained in a fluid to be measured flowing in the space 104 for storing a substance to be measured, the organic substances are decomposed by the photocatalytic activity. Therefore, even if ion exchange is performed on the electrode surfaces during the measurement of conductivity, the nonconductive organic substances are prevented from adhering or being adsorbed onto the electrode surfaces. As a result, a periodical cleaning of the electric surfaces is not required any more, and conductivity can be measured stably and accurately at all times without any cleaning. Further, repeatability of such a high-accuracy measurement can also be ensured.

Further, if a titanium oxide coating layer is provided on the surface of glass plate 108 on its side facing the space 104 for storing a substance to be measured, the adhesion or adsorption of organic substances to this surface side is also prevented, and accumulation of the organic substances in the space 104 for storing a substance to be measured is prevented, thereby maintaining the high-accuracy measurement.

Although the difference conductivity meter used in an ion concentration meter according to the present invention has been explained in detail, in the present invention, the above-described difference conductivity meter is incorporated into the ion concentration meter. With respect to the effectiveness according to use of the difference conductivity meter for the measurement of ion concentration in the present invention, namely, with respect to the essential technical concept according to the present invention, the ion concentration meter according to the present invention will be explained mainly as to experiments for confirming the effectiveness.

As described above, since the difference conductivity meter used in the present invention can have an electrode constitution using electrodes covered with titanium oxide layers on their surfaces and being used under a condition of light irradiation and has an apparatus constitution including a specified differential measurement circuit, an extremely minute change in conductivity can be stably detected particularly in a system such as one containing water-soluble organic substances with a high conductivity. The ion concentration meter according to the present invention determines this change in conductivity as a change in ion concentration.

For example, although a stable measurement has been almost impossible in a brine containing organic substances in the conventional technology because the dirt of electrodes is great, as aforementioned, by employing a constitution wherein electrode surfaces are covered with titanium oxide layers and the layers are irradiated with light having a wavelength of about 350 nm capable of activating the titanium oxide, the electrode surfaces are remarkably enhanced in hydrophilicity (super-hydrophilic interfaces are formed) and they have an oxidizing decomposition property for organic substances and the like by the photocatalytic activity, and therefore, the adhesion of organic substances and the like onto the electrode surfaces do not occur. Further, because the hydration structure of ions is not broken at the interfaces, an extremely high stability can be ensured as compared with conventional electrode materials. In particular, by forming two conductivity measuring cells each having a constant AC voltage drive and AC current amplification system using three electrodes, and by using the differential measurement circuit, an almost ultimate high-sensitivity and high-stability difference conductivity meter utilizing the characteristics of the electrode material can be constituted.

Figure 9:
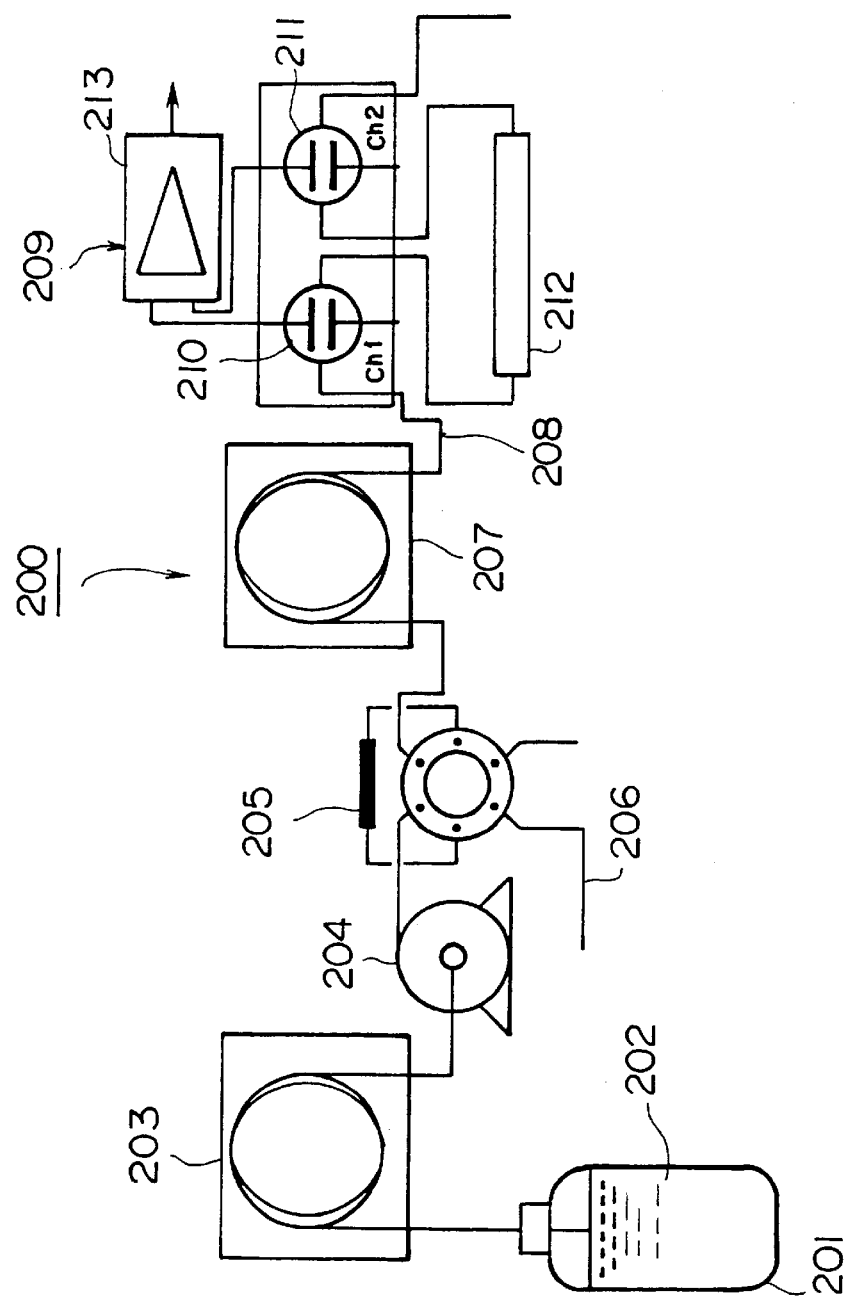
FIG. 9 is a schematic view of an experimental apparatus for confirming the effectiveness of an ion concentration meter according to the present invention.

In order to confirm the effectiveness of use of such a difference conductivity meter for the measurement of a change in ion concentration, the following experiment was carried out. FIG. 9 shows a schematic constitution of the experimental apparatus. In the experimental ion concentration meter 200 shown in FIG. 9, brine 202 in a cooling water producing system is stored in a sample bottle 201 as a sample, and the sample brine is supplied to a sample injection valve 205 by a pump 204 through a degasifier 203. The sample injection valve 205 supplies a predetermined constant volume of the supplied sample brine or a sample supplied from another system 206 to a sample measuring flow path 208 through a degasifier 207. In this sample measuring flow path 208, a difference conductivity meter 209 such as one aforementioned is disposed. The difference conductivity meter 209 has two conductivity measuring cells 210, 211 (channel ch1 and channel ch2), and a time delay column 212 having a predetermined capacity is interposed between both conductivity measuring cells 210, 211. A signal of a difference between detection signals from both conductivity measuring cells 210, 211, that is, a signal of a difference in conductivity between the positions of both conductivity measuring cells 210, 211, as aforementioned, is output at a high accuracy from an amplifier 213 of the difference conductivity meter 209.

Where, the degasifiers 203, 207 are provided particularly to stabilize the difference conductivity meter 209. Namely, they are used for preventing the swing of the conductivity caused by passing of micro bubbles. By providing the time delay column 212, a conductivity at a constant interval of time can be detected as a difference between conductivities from the channels ch1 and ch2, as long as the time delay column 212 has a constant volume and a constant length and the sample is sent at a constant flow rate for detecting a change in conductivity with time.

The sample brine used in this experiment has a conductivity of about 3000 $\mu$S and is a sample containing isopropyrene glycol at a content of 30 to 40% as an anticorrosive and having a pH of about 10. An extra pure ammonia solution was added to this sample to adjust the ammonia concentration, and the change in conductivity of the sample was determined.

Figure 10:
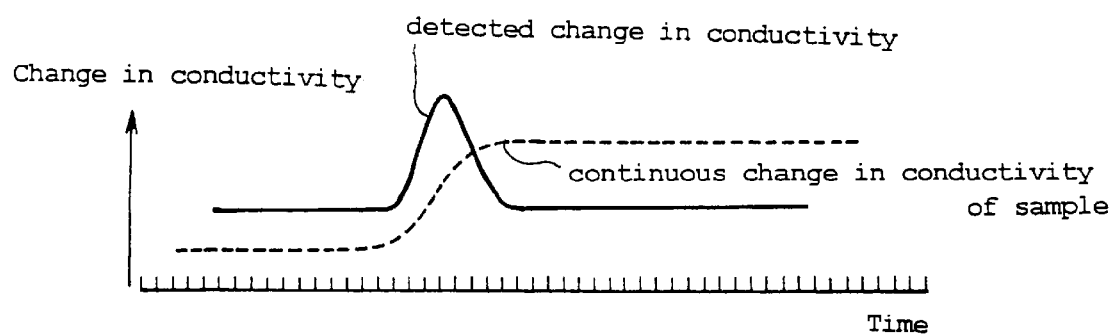
FIG. 10 is a graph of a change in conductivity showing an example of the result of the experiment carried out by the experimental apparatus shown in FIG. 9.
Figure 11:
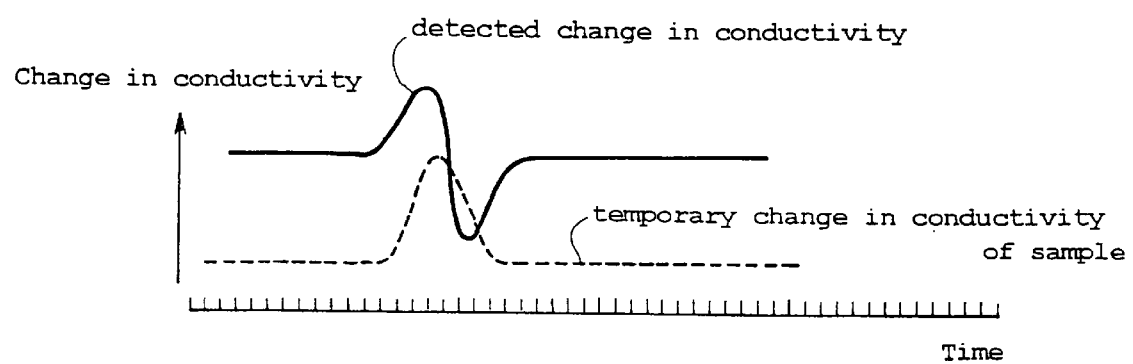
FIG. 11 is a graph of a change in conductivity showing another example of the result of the experiment carried out by the experimental apparatus shown in FIG. 9.

As aforementioned, a difference in conductivity between the positions of conductivity measuring cells 210, 211 is measured at a high accuracy by the difference conductivity meter 209. The relationship between the change in concentration of ammonia in the sample brine and the detected output obtained in the above-described experiment is shown in FIGS. 10 and 11. In a case where the concentration of ammonia in the sample brine continuously changes, when the time differential thereof is taken, the change in concentration of ammonia is detected as a single peak as shown in FIG. 10. On the other hand, in a case where the concentration of ammonia changes temporarily, the change in concentration of ammonia is detected as an overshoot wave form as shown in FIG. 11. In a case where a conventional-type conductivity meter is used, when the base conductivity of a sample is very great, it is impossible to detect such a minute change in concentration of ammonia.

In the above-described experiment, a change in ion concentration (concentration of ammonia) up to a minute value could be detected at high accuracy and sensitivity. In this experiment, 29% extra pure ammonia solution on the market was diluted by ultrapure water to prepare a solution with an ammonia content of 8700 ppm. A constant volume of this master was added to the sample brine bottle 201 shown in FIG. 9. Where, the volume of the brine before addition had been determined.

Figure 12B:
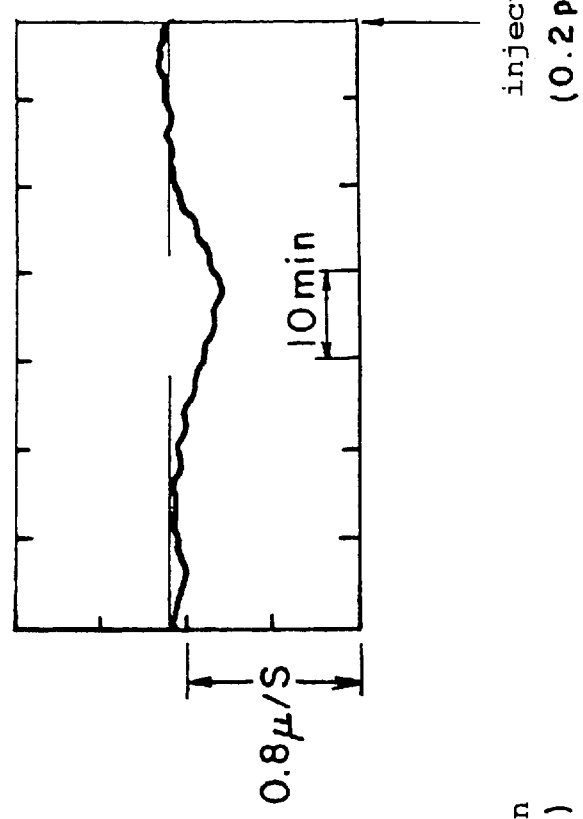
FIGS. 12A and 12B are measurement charts of changes in conductivity (changes in concentration of ammonia) in the result of the experiment carried out by the experimental apparatus shown in FIG. 9, showing examples corresponding to the change shown in FIG. 10.
Figure 12A:
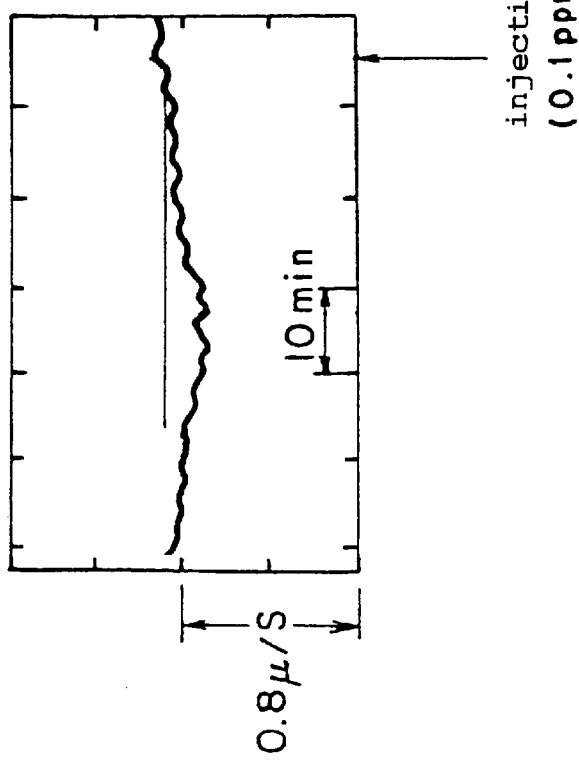
Figure 13:
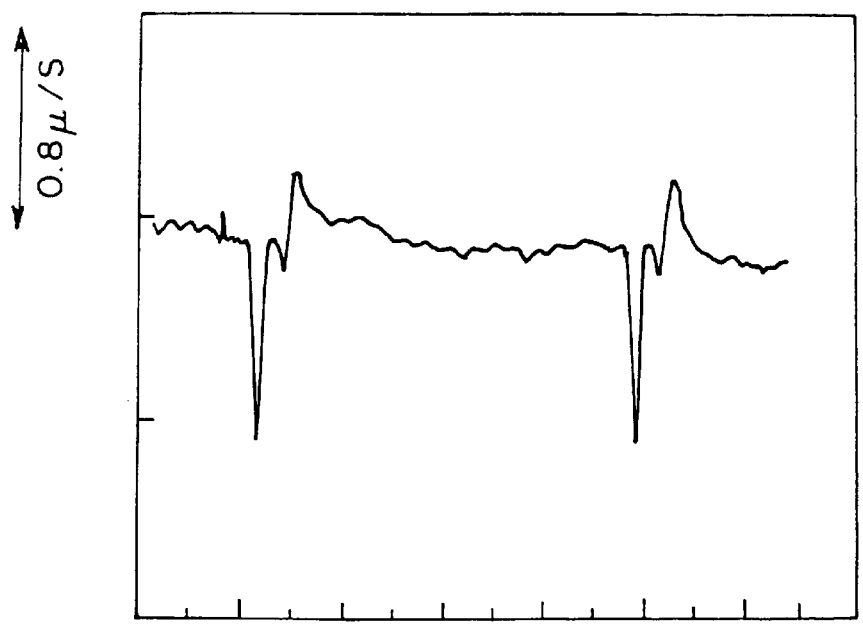
FIG. 13 is a measurement chart of a change in conductivity (a change in concentration of ammonia) in the result of the experiment carried out by the experimental apparatus shown in FIG. 9, showing an example corresponding to the change shown in FIG. 11.

Since the concentration of ammonia in the sample brine bottle 201 is considered to become uniform almost immediately after the addition, a concentration gradient is generated in the tube along with the supply of the solution by the pump. The change in concentration of ammonia can be detected by determining a difference at a time delay longer than the concentration gradient. FIGS. 12A and 12B show examples of the measurement (charts of the result of the experiment). As understood from these Figures, as the change in concentration of ammonia corresponding to the change in conductivity ($\mu$S: micro Siemens), a change of 0.1 to 0.2 ppm can be sufficiently measured. The examples of the measurement shown in these Figures indicate the aspect wherein the concentration of ammonia in the sample changes relatively slowly and continuously and the conductivity changes in correspondence with the change of the concentration of ammonia, as shown in the aforementioned FIG. 10. FIG. 13 shows an example of the measurement wherein the concentration of ammonia in the sample changes relatively quickly and temporarily and conductivity changes in correspondence with the change of the concentration of ammonia, as shown in the aforementioned FIG. 11.

Figure 14:
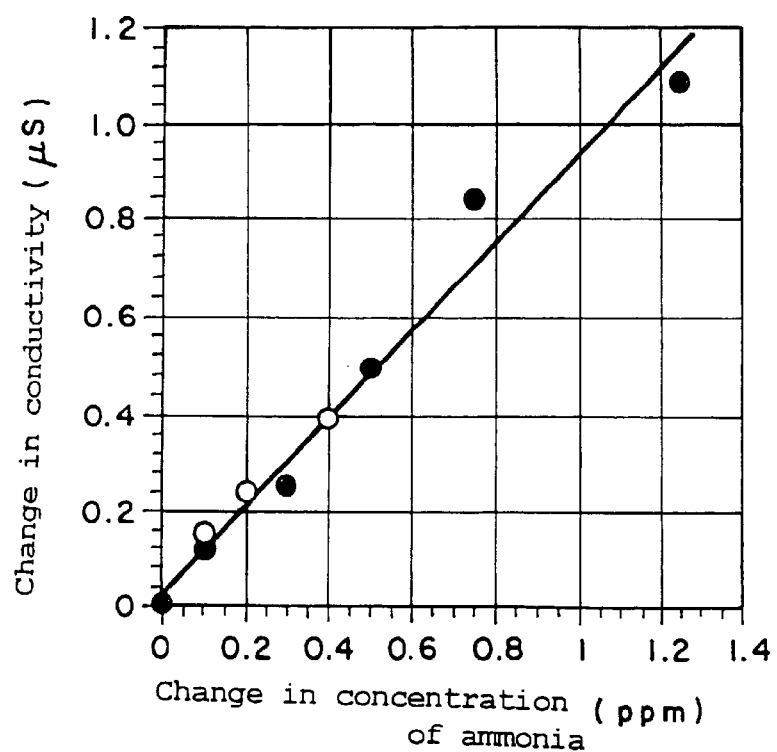
FIG. 14 is a graph showing a correlation between a change in conductivity and a change in concentration of ammonia.

The correlation between a change in conductivity and a change in ion concentration can be determined by variously changing the ion concentration of a sample in a similar experiment. FIG. 14 shows a graph plotted with the relationship between the concentration of ammonia (a range lower than about 1 ppm) measured by a method similar to that shown in FIG. 12 and a peak height ($\mu$S) of conductivity such as that shown in FIG. 10. In the experiment for determining the relationship shown in FIG. 14, only the samples were changed, the measuring apparatus, the pump and the like were left until they reached at their equilibrium conditions after deposition of power (about 2 hours for stabilizing the apparatus), and thereafter, the measurement was carried out. The interval between the measurements of the white circular marks and the black circular marks was one week. Where, as the pump used for sending the solution, a pump "CCPM" for liquid chromatograph (manufactured by Toso Corporation) was used at its reciprocal single cylinder mode.

As shown in FIG. 14, as the result that the repeatability was investigated at an interval of one week, it was understood that the data were plotted on a single straight characteristic line with no problem. Namely, it was confirmed that the change in concentration of ammonia and the change in conductivity were in an almost complete correlation in the region of a minute change in concentration of ammonia. Further, even in a system indicating a temporary change as shown in FIG. 11, it is understood that the measurement can be easily carried out from this result, if the delayed time and the amount of injection are appropriately adjusted.

Thus, in the measurement principle according to the present invention that the change in ion concentration is determined by measuring the change in conductivity, it becomes clear that even a minute change in ion concentration can be measured at extremely high accuracy and sensitivity.

Next, examples applying the ion concentration meter according to the present invention to actual apparatuses will be explained.

Figure 15:
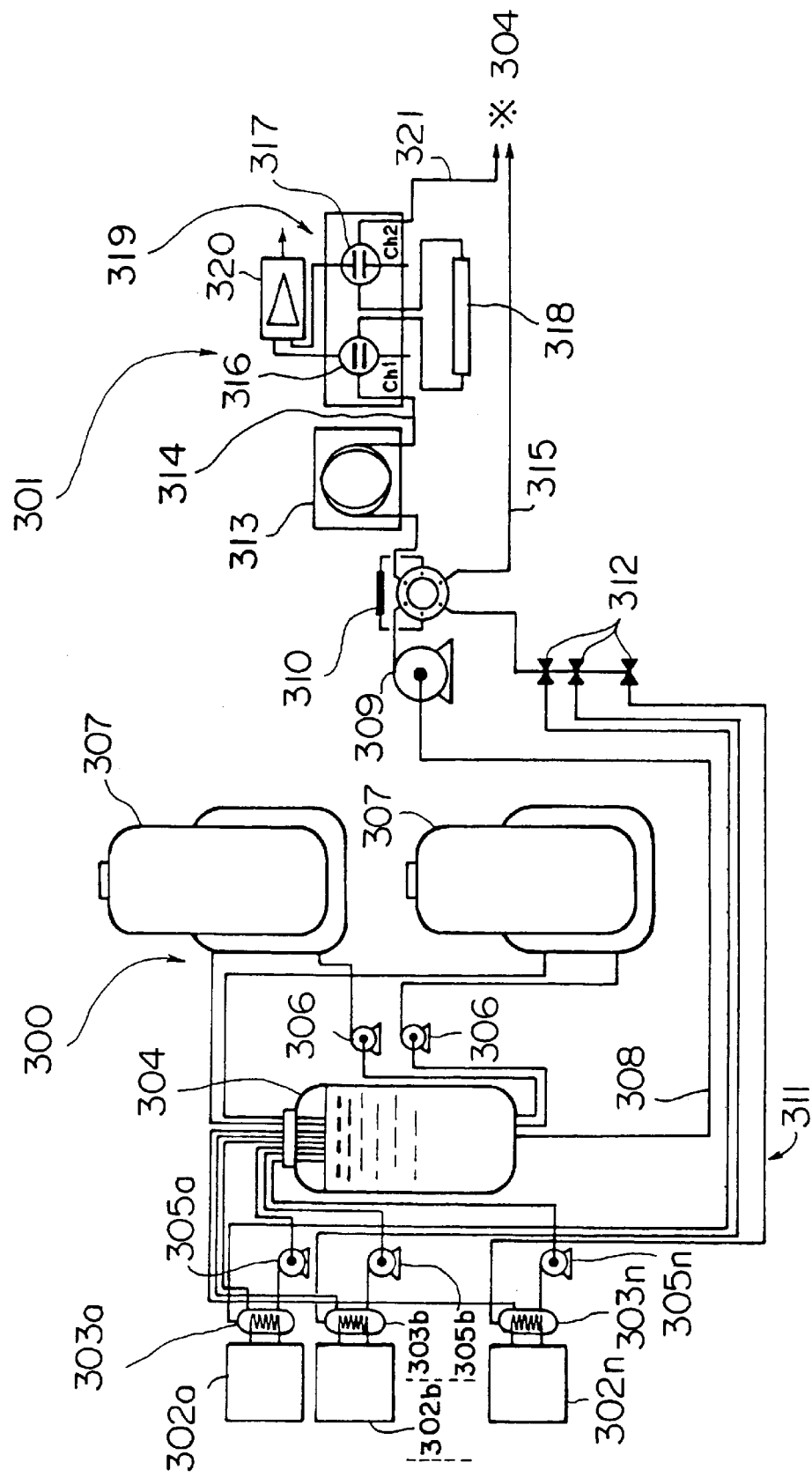
FIG. 15 is a schematic view showing an example that applies an ion concentration meter according to the present invention to a cooling water producing system.

FIG. 15 shows a case where an ammonia concentration measuring apparatus provided as the ion concentration meter according to the present invention is applied to a system for measuring the concentration (change in concentration) of ammonia leaked into a brine from the side of a refrigerator in a cooling water producing system. In FIG. 15, an ammonia concentration measuring apparatus 301 provided as the ion concentration meter according to the present invention is incorporated into a cooling water producing system 300. A plurality of refrigerators 302a . . . 302n and heat exchangers 303a . . . 303n and a surge tank 304 are provided in the cooling water producing system 300, the brines supplied from the surge tank 304 by pumps 305a . . . 305n are cooled in the respective heat exchangers 303a . . . 303n by heat exchange with refrigerants containing ammonia of the sides of the respective refrigerators 302a . . . 302n, and the cooled brines are circulated into the surge tank 304. The cooled brine in the surge tank 304 is sent to respective target tanks 307 for cooling the target tanks via respective pumps 306. The cooling water is sent to a predetermined use point directly from each target tank 307 or further via a pump.

In such a cooling water producing system 300, particularly since a leakage of ammonia from the sides of refrigerators 302a . . . 302n into the brine at the portions of heat exchangers 303a . . . 303n is considered to be a problem, it is required to monitor and detect this at a high accuracy. To detect such a leakage of ammonia, the ammonia concentration measuring apparatus according to the present invention can be applied.

Namely, in the embodiment shown in FIG. 15, the conductivity of the sample brine extracted from the discharge port and the like of each of the heat exchangers 303a . . . 303n is compared with the conductivity of the brine extracted from the surge tank 304, referring to the conductivity of the brine from the surge tank 304 as a base value. In the example depicted in the Figure, the brine as a base is taken from the surge tank 304 by a pump 309 through a base line 308, it is supplied to an injection valve 310, and the sample brines are supplied to the injection valve 310 from the respective heat exchangers 303a . . . 303n through sample taking lines 311. In this embodiment, the sample brines from the respective sample taking lines 311 are supplied to the injection valve 310 selectively by switching a switch valve 312. Therefore, the respective sample brines from the respective sample taking lines 311 can be measured repeatedly at a certain time interval.

The respective sample brines in the injection valve 310 are conveyed by the base brine from the surge tank 304, and they are supplied to a sample measuring flow path 314 of the ammonia concentration measuring apparatus 301 through a degasifier 313 as samples to be measured for determining a change in concentration of ammonia. The brine which has not been used for the measurement is returned to the surge tank 304 through a return line 315, as it is.

Two conductivity measuring cells 316, 317 are arranged in series in the sample measuring flow path 314, and therebetween a time delay column 318 having a predetermined capacity is interposed. Thus, a difference conductivity meter 319 is constituted which outputs a difference between the signals themselves detected by conductivity measuring cells 316, 317 as a difference in conductivity of the sample between the positions of the conductivity measuring cells 316, 317, and the signal is output via an amplifier 320. From this output from the difference conductivity meter 319, similarly to that shown in FIG. 14, the change in concentration of ammonia in the sample is derived based on a predetermined correlation between a change in conductivity of the sample and a change in concentration of ammonia to be detected in the sample.

By such a constitution, the sample brines from the respective sample taking lines 311 are sent by the base brine from the surge tank 304, thereby detecting the change in concentration of ammonia at a high sensitivity. Moreover, because the change in concentration of ammonia in the surge tank 304 can almost be ignored by altering the length of the time delay column 318, etc., the leakage of ammonia can be detected at high accuracy and sensitivity regardless of the change in concentration of the base.

However, as shown in FIG. 15, the time for one measurement depends on the flow rate of the pump, the dead volume and the like of the apparatus (particularly, depends on the volume of the degasifier), and in the system shown in FIG. 15, it took about 5 minutes to complete one measurement. Namely, if there are three refrigerators, each refrigerator is to be checked at an interval of at least 15 minutes. In a case where a continuous measurement is required, a system described later as shown in FIG. 16 can be employed.

As understood from FIG. 15, since the brines sampled through the respective sample taking lines 311 are returned to the surge tank 304 via a return line 321 or the return line 315, it does not occur that they are discharged outside the system. Further, the difference conductivity meter 319 is extremely stable, and for example, it can be stably operated by an overhaul at a frequency of about once per a year. As the present actual result, the apparatus has been used at a condition of maintenance free for about 8 months.

Figure 16:
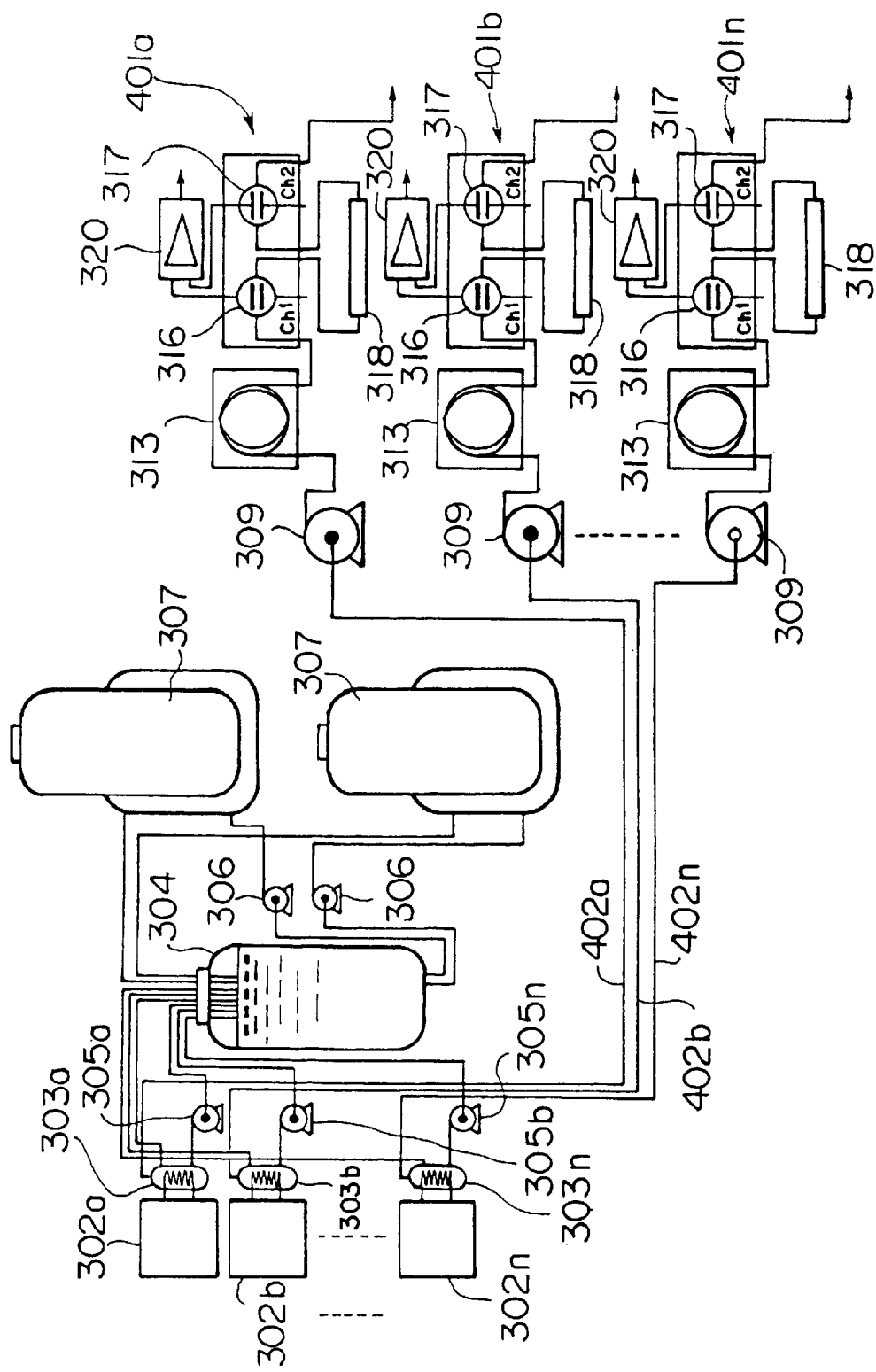
FIG. 16 is a schematic view showing another example that applies an ion concentration meter according to the present invention to a cooling water producing system.

FIG. 16 shows an example of a multi-channel measuring system wherein a sample measuring flow path having two conductivity measuring cells is disposed relative to each of a plurality of sample sources. In this system, respective difference conductivity meters 401a . . . 401n are provided for respective sample taking lines 402a . . . 402n, and a base sample line from surge tank 304, a switching valve and an injection valve are not provided. Other constitutions are substantially the same as those shown in FIG. 15.

In such a multi-channel measuring system, it is possible to determine the changes in concentration of ammonia of the respective sample brines from the respective sample taking lines 402a . . . 402n, independently from each other directly and continuously. In a case Where the velocity or volume of leakage of ammonia is to be considered, it is preferable to thus dispose difference conductivity meters one by one in correspondence with the respective refrigerators and continuously monitor.

Figure 17:
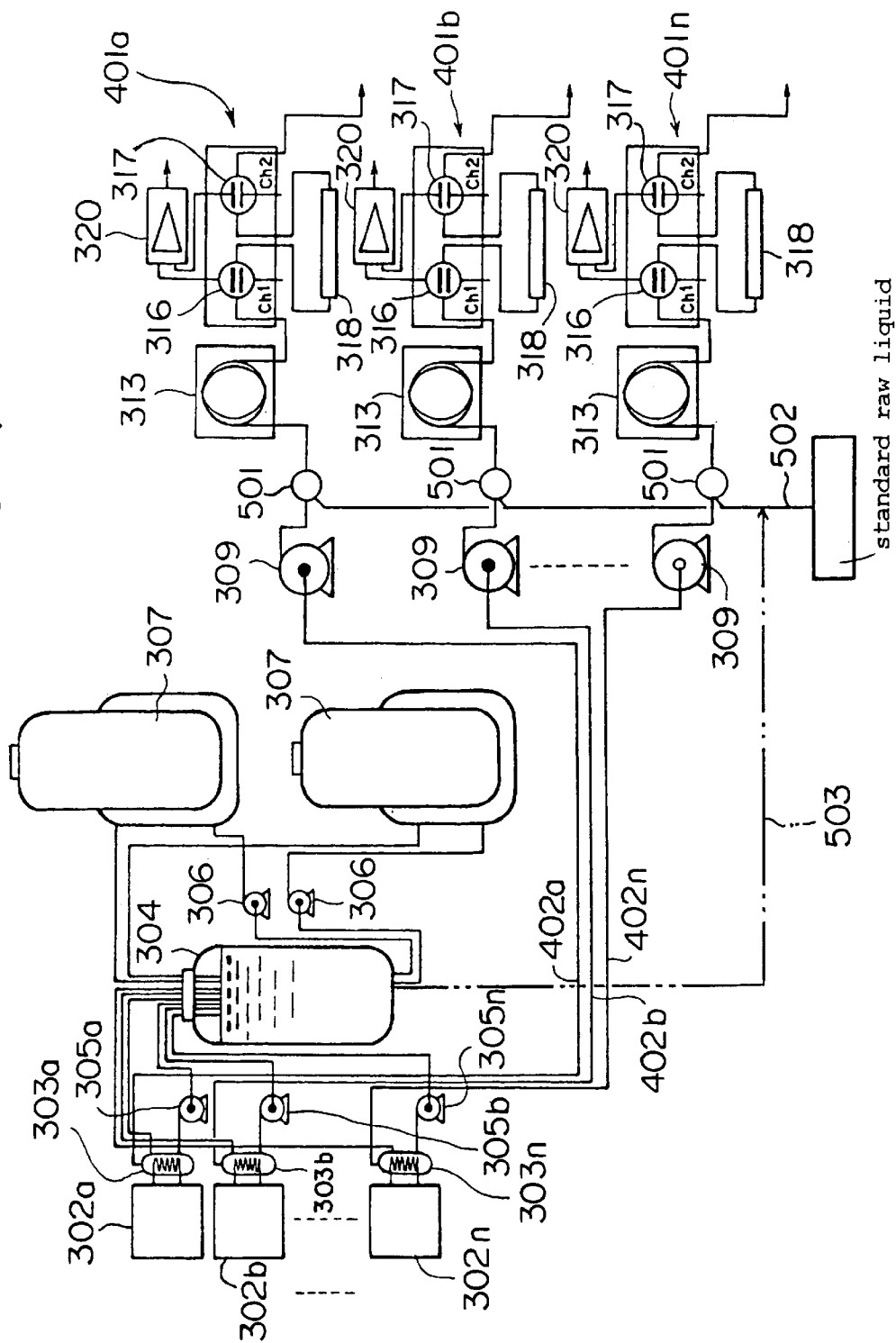
FIG. 17 is a schematic view showing a further example that applies an ion concentration meter according to the present invention to a cooling water producing system.

Further, FIG. 17 shows an example of a measuring system where a standard raw liquid is injected, for example, as an example in which means for injecting a standard raw liquid is added to the system shown in FIG. 16. In the multi-channel measuring system shown in FIG. 17, as compared with the system shown in FIG. 16, an injection valve 501 is interposed between each pump 309 and each degasifier 313, and to each injection valve 501, standard raw liquid injecting means 502 for supplying a standard raw liquid used as a carrier fluid (a standard raw liquid prepared at a constant ammonia concentration, or a standard raw liquid which substantially does not contain ammonia) is connected. The standard raw liquid is injected into the sample brine supplied from each of sample taking lines 402a . . . 402n by each injection valve 501, and the sample mixed with the brine and the standard raw liquid is served to the measurement of change in ammonia concentration by each of difference conductivity meters 401a . . . 401n.

In such a constitution, since the change in ammonia concentration of the sample can be always determined based on the standard value of the standard raw liquid, it becomes possible to determine the change and to further increase the measurement accuracy even in a case where a change in concentration of ammonia of a sample is very small but the change is continuously maintained and therefore the change reaches a level to be detected after a relatively long period of time, if such a change is measured by utilizing the time delay column 318, it must be a time delay column set with a fairly long time, and therefore the measurement using such a time delay column is not practical. Further, if the supply of the standard raw liquid is stopped, the system becomes the same system as that shown in FIG. 16.

In the measuring system shown in FIG. 17, as depicted by the two-dot chain line in FIG. 17, it is possible that a standard raw liquid supply system 503 from the surge tank 304 is provided instead of the standard raw liquid supply system 502 and the raw liquid therefrom is used as the carrier fluid. Namely, because the capacity of the surge tank 304 is great, the concentration of ammonia of the raw liquid in the surge tank 304 does not rapidly change so much and it is considered to be almost constant, and therefore, the raw liquid can be used as the carrier fluid.

Although the above-described example of application of an ion concentration meter according to the present invention has been explained as an application to the measurement of a change in concentration of ammonia in a cooling water producing system having a refrigerator, the application of the ion concentration meter according to the present invention is not limited thereto, it can also be applied to any field requiring the measurement of a minute change in concentration of ions such as sodium, chlorine, calcium, potassium, carbonate, silica, magnesium and sulphate ions except ammonia. For example, the ion concentration meter can also be applied to the measurement of a minute change in concentration of ammonia in the water for cleaning air in a clean room, the measurement of kinds of ions contained in a condensate in a power plant, the measurement for monitoring a leakage of sea water into the condensate and the like. Further, it can also be applied to the measurement of a change in ion concentration of a fluid to be heat exchanged in a heat exchange system or the measurement of a change in ion concentration of a usual diluted or mixed solution.

Figure 18:
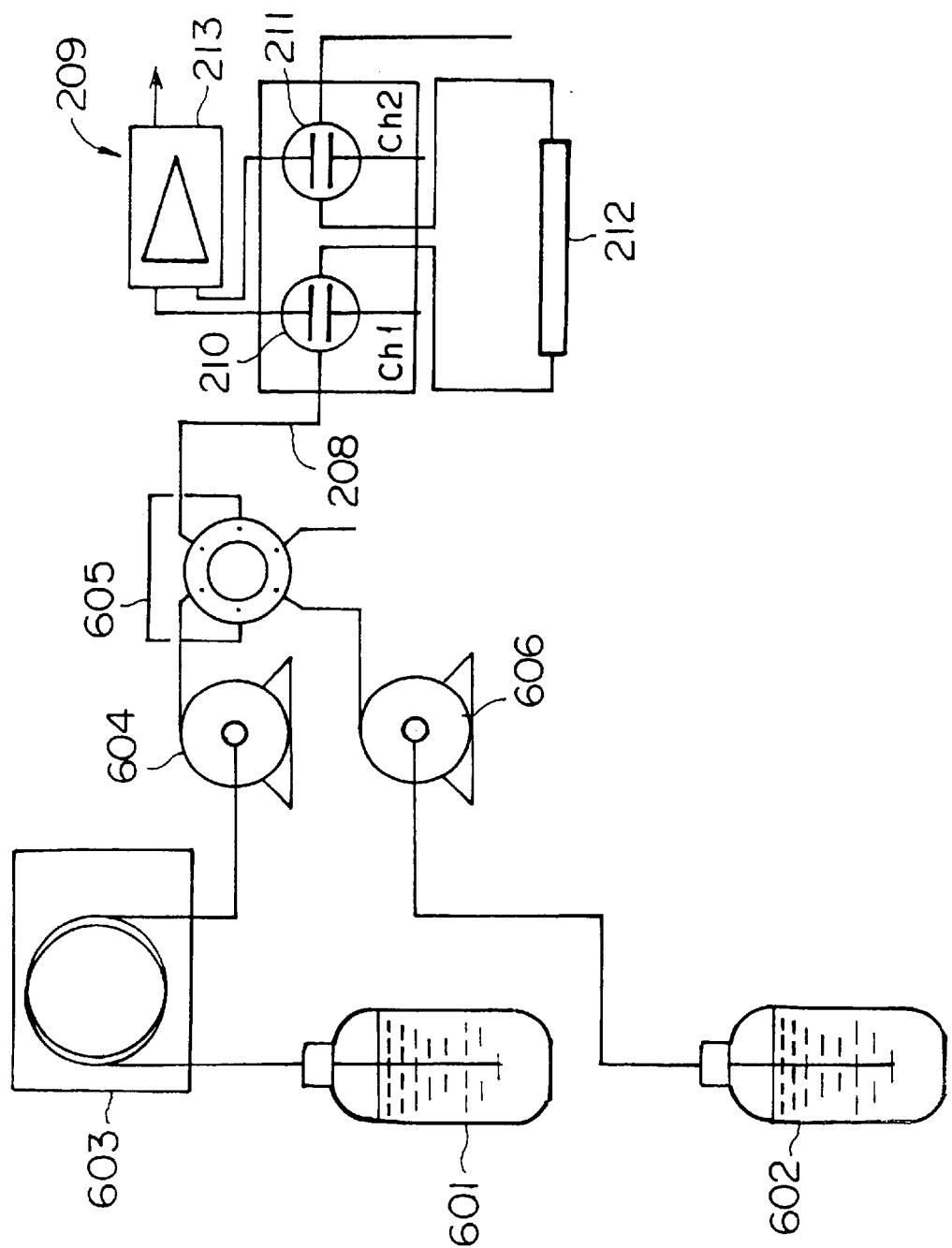
FIG. 18 is a schematic view of an experimental apparatus for investigating the performance of an ion concentration meter according to the present invention.

FIG. 18 shows an example of a constitution of an experimental apparatus for continuously monitoring and measuring a water quality. In FIG. 18, provided are a sample bottle 601 for storing a purified water (conductivity: 2.3 $\mu$S/cm) as a standard liquid and a sample bottle 602 for storing a potassium chloride solution as a sample solution. Using a difference conductivity meter 209 similar to that shown in FIG. 9, the purified water from the sample bottle 601 was continuously sent to a sample injection valve 605 via a degasifier 603 and a pump 604, and therefrom the standard liquid was continuously supplied to the difference conductivity meter 209. Relative to this supply system, respective potassium chloride solutions having concentrations of potassium chloride of 5 ppb, 10 ppb, 32.5 ppb and 75 ppb and a blank water having a concentration of potassium chloride of 0 ppb (that is, substantially the same purified water as the standard liquid) were discontinuously supplied to the sample injection valve 605 via a pump 606, and the solution mixed with the standard liquid and the sample was continuously supplied to the difference conductivity meter 209.

Figure 19:
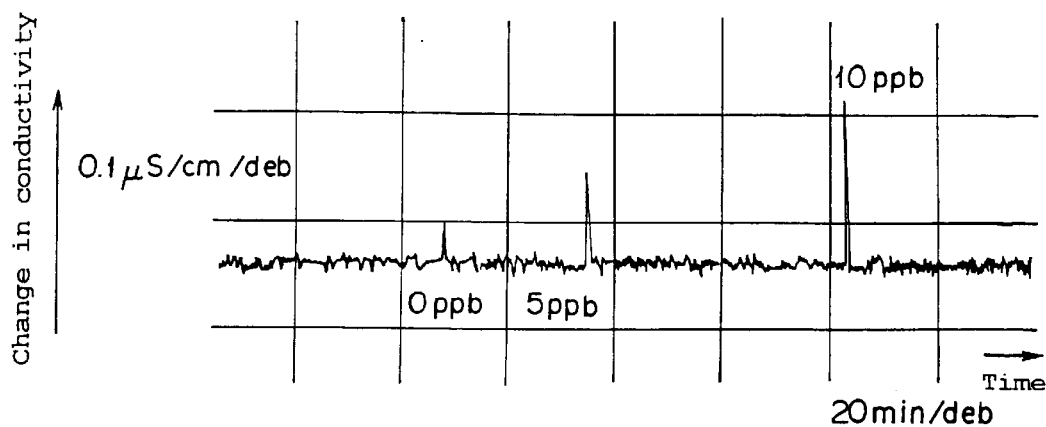
FIG. 19 is a measurement chart of a change in conductivity showing the result to the experiment carried out by the apparatus shown in FIG. 18.

FIG. 19 shows the result of the measurement of the change in conductivity in the above-described experiment (charts in the cases of 0 ppb, 5 ppb and 10 ppb). As shown in FIG. 19, it is understood that an extremely minute change in concentration of potassium chloride could be determined as the change in conductivity at high accuracy and sensitivity. Where, the reason why a change exhibited even in the case of the sample at 0 ppb is considered that, because a degasifier was not provided on the sample supply side, gas components such as $CO_2$ contained in the sample at a fine content could not be removed, and it influenced the measurement.

Figure 20:
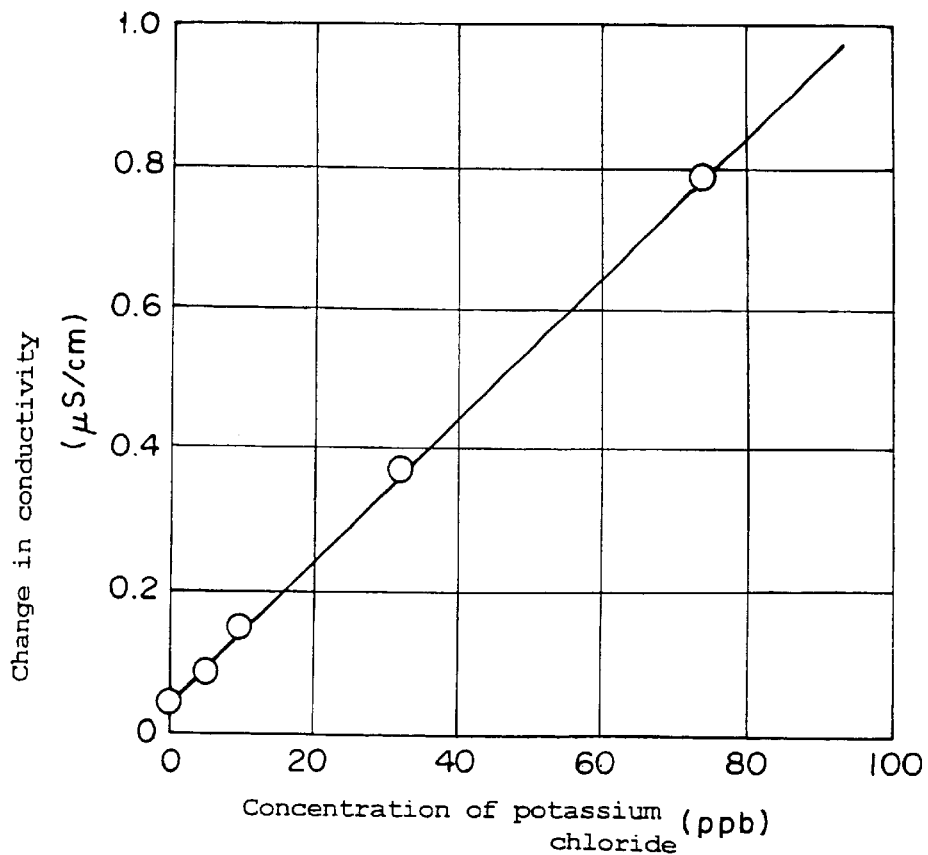
FIG. 20 is a graph showing a relationship between a concentration of potassium chloride and a change in conductivity obtained by plotting the result of the experiment carried out by the apparatus shown in FIG. 18.

FIG. 20 shows the result of the measurement for determining the correlation between the concentrations of potassium chloride from 0 to 75 ppb and the corresponding changes in conductivity ($\mu$S/cm). As shown in FIG. 20, the correlation is expressed by a complete straight line, and it is understood that a change in ion concentration up to a minute change can be determined with high accuracy and sensitivity by the ion concentration meter according to the present invention.

Thus, according to the present invention, since the ion concentration meter is constituted using a high-sensitivity difference conductivity meter, a change in ion concentration of a sample can be determined with extremely high accuracy and sensitivity, while a continuation measurement can be easily carried out. Further, in this ion concentration meter, chemicals and reaction apparatuses for the measurement are not required as in the conventional technology, and the measurement itself and the operation thereof are very simple. The sample used for the measurement can be returned directly to an original line.

Further, the ion concentration meter according to the present invention is simple in structure and can be manufactured at a low cost. Moreover, if the electrodes utilizing the photocatalytic activity of titanium oxide is employed, dirt of the electrodes does not occur, and free maintenance for the meter can also be achieved.

Furthermore, many requirements from a multi-channel switching type to a multi-channel continuous monitoring type can be accepted flexibly and easily.

In the present invention, the structure of the portion of the conductivity measuring cell is not limited to that shown in FIG. 7, and, for example, it can also be constructed as shown in FIG. 21. In a conductivity measuring cell 121 shown in FIG. 21, three electrodes 122*a*, 122*b*, 122*c* are provided, and for example, the electrode 122*a*, 122*b* on both sides are constituted as power supply electrodes connected to a power source, and the electrode 122*c* disposed between them is constituted as a detection electrode functioning as a sensor for detecting a conductivity. Through holes 123*a*, 123*b*, 123*c* are opened at the central portions of the respective electrodes 122*a*, 122*b*, 122*c*, and titanium oxide layers are provided on the inner surfaces of the respective holes 123*a*, 123*b*, 123*c*. Spacers 124*a*, 124*b*, 124*c*, 124*d* made of a light transmitting insulation material (for example, 4-fluoride ethylene) are disposed on both sides of the respective electrodes 122*a*, 122*b*, 122*c*, and the respective electrodes and spacers are stacked alternately. Through holes 125*a*, 125*b*, 125*c*, 125*d* are opened also in the central portions of spacers 124*a*, 124*b*, 124*c*, 124*d*, respectively. Support materials 126*a*, 126*b* are disposed outside of spacers 124*a*, 124*d* positioned at both sides, and a stacked body comprising the electrodes 122*a*, 122*b*, 122*c* and the spacers 124*a*, 124*b*, 124*c*, 124*d* are sandwiched from both sides by the support materials. Through holes 127*a*, 127*b* are opened also in the central portions of the respective support materials 126*a*, 126*b*, and into the holes 127*a*, 127*b*, one end of a tube 128*a* for introducing a fluid to be measured, and one end of a tube 128*b* for discharging the fluid are inserted and fixed, respectively.

A flow path of a fluid to be measured is formed by holes 125*a*, 123*a*, 125*b*, 123*c*, 125*c*, 123*b*, 125*d* connected by stacking the electrodes 122*a*, 122*b*, 122*c* and the spacers 124*a*, 124*b*, 124*c*, 124*d*. A fluid to be measured introduced through tube 128*a* is discharged through tube 128*b*, after flowing inside of this flow path. These tubes 128*a*, 128*b* are composed of a light transmitting material (for example, 4-fluoride ethylene), and an ultraviolet ray with a predetermined wavelength is irradiated from a black light 129 provided as means for irradiating light. As the ultraviolet ray irradiated repeats diffusion and reflection in tubes 128*a*, 128*b* as well as transmits the tubes, the ultraviolet ray is guided along the tubes 128*a*, 128*b*, and guided to the inner surfaces formed by titanium oxide layers in the respective electrodes 122*a*, 122*b*, 122*c* from the portions of holes 127*a*, 127*b* at both sides. Further, as the respective spacers 124*a*, 124*b*, 124*c*, 124*d* are also composed of a light transmitting material, the ultraviolet ray from the black light 129 is irradiated to the inner surfaces of electrodes 122*a*, 122*b*, 122*c* after transmitting each spacer while utilizing diffusion and reflection. Especially, by forming each electrode and spacer to be relatively thin (for example, the thickness of each electrode is about 0.2 mm, and the thickness of each spacer is about 1 mm), because the flow path formed by the respective electrodes and spacers becomes relatively short, even if a particular light transmitting material such as an optical fiber is not used, a sufficient amount of light for measurement is irradiated onto predetermined electrode surfaces by the light guiding along light transmitting tubes 58*a*, 58*b* as described above, and by the light guiding through light transmitting spacers 124*a*, 124*b*, 124*c*, 124*d*. Therefore, in this embodiment, a simpler and smaller unit can be constructed.

INDUSTRIAL APPLICATIONS OF THE INVENTION

In the ion concentration meter according to the present invention, because changes in concentration of various ions can be measured at extremely high accuracy and sensitivity, the meter can be suitably employed in any system requiring the detection of change in ion concentration, and a minute change in concentration, which has been impossible to be detected, can be detected accurately. By such a high-accuracy measurement of ion concentration, it becomes possible to prevent a great leakage of impurities into a system or an undesirable change in ion concentration in the system in advance, and further, it becomes possible to maintain and control the ion concentration in any system to a desired value at all times.

What is claimed is:

1. An ion concentration meter characterized in that said ion concentration meter comprises a difference conductivity meter wherein two conductivity measuring cells each having at least two electrodes are arranged in series in a flow path of a sample to be measured so that a sample being sent makes contact with the cells in sequence, said difference conductivity meter producing a difference between signals themselves detected by the conductivity measuring cells as a difference in conductivity of the sample between the positions of the conductivity measuring cells, and said ion concentration meter deriving a change in ion concentration of the sample from the output from said difference conductivity meter, based on a predetermined correlation between a change in conductivity of the sample and a change in concentration of an ion to be detected in the sample, wherein a time delay column having a predetermined capacity is interposed between said two conductivity measuring cells arranged in said flow path of the sample to be measured.

2. The ion concentration meter according to claim 1, wherein said ion concentration meter further comprises means for sending a standard raw liquid to said flow path of the sample to be measured as a carrier fluid, and means for injecting a sample to be measured with respect to a change in ion concentration into said carrier fluid.

3. The ion concentration meter according to claim 1, wherein each of said conductivity measuring cells has three electrodes, said three electrodes include a conductivity detection electrode and two AC current supply electrodes disposed on both sides of said conductivity detection electrode at respective distances, and an AC current of the same phase is applied to said two AC current supply electrodes.

4. The ion concentration meter according to claim 1, wherein each of said conductivity measuring cells has three electrodes, said three electrodes include a conductivity detection electrode, an AC current supply electrode disposed on one side of said conductivity detection electrode at a distance, and a grounded electrode disposed on the other side of said conductivity detection electrode at a distance.

5. The ion concentration meter according to claim 1, wherein said at least two electrodes of each of said conductivity measuring cells are constructed so that their electrode surfaces are formed by titanium oxide layers on surfaces of electrode bodies made of a conductive metal.

6. The ion concentration meter according to claim 5, wherein each conductivity measuring cell has a space for storing a substance to be measured which is defined between respective electrode surfaces of said at least two electrodes, and means for irradiating light onto the respective electrode surfaces.

7. The ion concentration meter according to claim 6, wherein light irradiated from said light irradiating means has a wavelength which brings about a photocatalytic activity of said titanium oxide layers.

8. The ion concentration meter according to claim 6, wherein said space for storing a substance to be measured is defined by a light transmitting material, and light from said light irradiating means is irradiated onto said electrode surfaces through said light transmitting material.

9. The ion concentration meter according to claim 8, wherein a titanium oxide coating layer capable of transmitting light is provided on a surface of said light transmitting material of its side facing said space for storing a substance to be measured.

10. The ion concentration meter according to claim 1, wherein said sample is collected from a brine in a cooling water producing system, and said ion concentration meter measures a change in concentration of ammonia which has leaked from the side of a refrigerator into said brine.

11. An ion concentration meter characterized in that said ion concentration meter comprises a difference conductivity meter wherein two conductivity measuring cells each having at least two electrodes are arranged in series in a flow path of a sample to be measured so that a sample being sent makes contact with the cells in sequence, said difference conductivity meter producing a difference between signals themselves detected by the conductivity measuring cells as a difference in conductivity of the sample between the positions of the conductivity measuring cells, and said ion concentration meter deriving a change in ion concentration of the sample from the output from said difference conductivity meter, based on a predetermined correlation between a change in conductivity of the sample and a change in concentration of an ion to be detected in the sample, wherein said ion concentration meter further comprises means for sending a standard raw liquid to said flow path of the sample to be measured as a carrier fluid, and means for injecting a sample to be measured with respect to a change in ion concentration into said carrier fluid.

12. The ion concentration meter according to claim 11, wherein each of said conductivity measuring cells has three electrodes, said three electrodes include a conductivity detection electrode and two AC current supply electrodes disposed on both sides of said conductivity detection electrode at respective distances, and an AC current of the same phase is applied to said two AC current supply electrodes.

13. The ion concentration meter according to claim 11, wherein each of said conductivity measuring cells has three electrodes, said three electrodes include a conductivity detection electrode, an AC current supply electrode disposed on one side of said conductivity detection electrode at a distance, and a grounded electrode disposed on the other side of said conductivity detection electrode at a distance.

14. The ion concentration meter according to claim 11, wherein said at least two electrodes of each of said conductivity measuring cells are constructed so that their electrode surfaces are formed by titanium oxide layer on surfaces of electrode bodies made of a conductive metal.

15. The ion concentration meter according to claim 14, wherein each conductivity measuring cell has a space for storing a substance to be measured which is defined between respective electrode surfaces of said at least two electrodes, and means for irradiating light onto the respective electrode surfaces.

16. The ion concentration meter according to claim 15, wherein light irradiated from said light irradiating means has a wavelength which brings about a photocatalytic activity of said titanium oxide layers.

17. The ion concentration meter according to claim 15, wherein said space for storing a substance to be measured is defined by a light transmitting material, and light from said light irradiating means is irradiated onto said electrode surfaces through said light transmitting material.

18. The ion concentration meter according to claim 17, wherein a titanium oxide coating layer capable of transmitting light is provided on a surface of said light transmitting material of its side facing said space for storing a substance to be measured.

19. The ion concentration meter according to claim 11, wherein said sample is collected from a brine in a cooling water producing system, and said ion concentration meter measures a change in concentration of ammonia which has leaked from the side of a refrigerator into said brine.

20. An ion concentration meter characterized in that said ion concentration meter comprises a difference conductivity meter wherein two conductivity measuring cells each having at least two electrodes are arranged in series in a flow path of a sample to be measured so that a sample being sent makes contact with the cells in sequence, said difference conductivity meter producing difference between signals themselves detected by the conductivity measuring cells as a difference in conductivity of the sample between the positions of the conductivity measuring cells, and said ion concentration meter deriving a change in ion concentration of the sample from the output from said difference conductivity meter, based on a predetermined correlation between a change in conductivity of the sample and a change in concentration of an ion to be detected in the sample, wherein said sample is collected from a brine in a cooling water producing system, and said ion concentration meter measures a change in concentration of ammonia which has leaked from the side of a refrigerator into said brine.

* * * * *

UNITED STATES PATENT AND TRADEMARK OFFICE
CERTIFICATE OF CORRECTION

PATENT NO. : 6,646,443 B2
DATED : November 11, 2003
INVENTOR(S) : Higo

It is certified that error appears in the above-identified patent and that said Letters Patent is hereby corrected as shown below:

Column 20,
Line 36, "oxide layer" should read -- oxide layers --.

Column 21,
Line 2, "producing difference" should read -- producing a difference --.

Signed and Sealed this

Fourteenth Day of March, 2006

JON W. DUDAS
*Director of the United States Patent and Trademark Office*